(12) United States Patent
King et al.

(10) Patent No.: US 7,718,649 B1
(45) Date of Patent: May 18, 2010

(54) PHYSICAL STATES OF A PHARMACEUTICAL DRUG SUBSTANCE

(75) Inventors: Clifford Riley King, Hendersonville, NC (US); David William Bristol, Mills River, NC (US); Vicki Haynes Audia, Mills River, NC (US); Joseph Pike Mitchener, Jr., Flat Rock, NC (US)

(73) Assignee: Pisgah Labs, Inc., Pisgah Forest, NC (US)

( * ) Notice: Subject to any disclaimer, the term of this patent is extended or adjusted under 35 U.S.C. 154(b) by 818 days.

(21) Appl. No.: 11/595,379

(22) Filed: Nov. 10, 2006

(51) Int. Cl.
*A61P 25/00* (2006.01)
*A61K 31/55* (2006.01)
*C07D 223/18* (2006.01)

(52) U.S. Cl. ...................... 514/217; 540/592
(58) Field of Classification Search ................. 514/217; 540/592
See application file for complete search history.

(56) References Cited

U.S. PATENT DOCUMENTS

| | | | |
|---|---|---|---|
| 1,461,407 A | 7/1923 | Trout | |
| 2,925,417 A | 2/1960 | Ekskager et al. | 260/240 |
| 3,326,896 A | 6/1967 | Holstius et al. | 260/239 |
| 3,502,661 A | 3/1970 | Kasubick et al. | 260/240 |
| 4,283,408 A | 8/1981 | Harata et al. | 424/270 |
| 5,120,850 A | 6/1992 | Bod et al. | 548/197 |
| 5,128,477 A | 7/1992 | Bod et al. | 548/197 |
| 5,225,205 A | 7/1993 | Orsolini | 424/489 |
| 5,232,919 A | 8/1993 | Scgeffker et al. | 514/212 |
| 5,271,946 A | 12/1993 | Hettche | 424/490 |
| 5,439,688 A | 8/1995 | Orsolini et al. | 424/489 |
| 5,445,832 A | 8/1995 | Orsolini et al. | 424/491 |
| 5,736,541 A | 4/1998 | Bunnell et al. | 514/220 |
| 5,776,885 A | 7/1998 | Orsolini et al. | 514/2 |
| 6,251,895 B1 | 6/2001 | Larsen et al. | 514/220 |
| 6,472,563 B1 | 10/2002 | Tanoury et al. | 564/216 |
| 6,720,453 B2 | 4/2004 | Tanoury et al. | 564/216 |
| 6,987,111 B2 | 1/2006 | Greco et al. | 514/253 |
| 7,022,698 B2 | 4/2006 | Hamied et al. | 514/220 |

FOREIGN PATENT DOCUMENTS

| | | |
|---|---|---|
| EP | 0137600 | 7/1984 |
| GB | 295656 | 11/1929 |

OTHER PUBLICATIONS

Hamlin, William E., Northam, Jack I., and Wagner, John G., Relationship Between In Vitro Dissolution Rates and Solubilities of Numerous Compounds Representative of Various Chemical Species, Mar. 31, 1965.

*Primary Examiner*—Brenda L Coleman
(74) *Attorney, Agent, or Firm*—Jospeh T. Guy; Nexsen Pruet, LLC

(57) ABSTRACT

An amorphous form of imipramine pamoate, morphologically pure forms, and mixtures of amorphous and morphologically pure imipramine pamoate characterized by differential scanning calorimetry, fourier transform infrared, and powder x-ray diffraction, and pharmaceutical compositions formed therefrom.

79 Claims, 21 Drawing Sheets

| | RT (min) | Area (V*sec) | % Area | Height (V) | % Height |
|---|---|---|---|---|---|
| 1 | 4.045 | 458 | 0.01 | 47 | 0.02 |
| 2 | 4.371 | 734 | 0.01 | 66 | 0.03 |
| 3 | 5.379 | 796 | 0.01 | 93 | 0.05 |
| 4 | 6.402 | 957 | 0.02 | 108 | 0.05 |
| 5 | 6.619 | 875 | 0.02 | 117 | 0.06 |
| 6 | 6.894 | 315 | 0.01 | 34 | 0.02 |
| 7 | 7.830 | 976 | 0.02 | 84 | 0.04 |
| 8 | 8.249 | 2097 | 0.04 | 187 | 0.09 |
| 9 | 12.949 | 576 | 0.01 | 47 | 0.02 |
| 10 | 14.216 | 1982 | 0.04 | 169 | 0.08 |
| 11 | 15.006 | 4623 | 0.09 | 434 | 0.21 |
| 12 | 15.555 | 5362242 | 99.52 | 204414 | 98.97 |
| 13 | 17.497 | 6982 | 0.13 | 412 | 0.20 |
| 14 | 18.099 | 3569 | 0.07 | 255 | 0.12 |
| 15 | 26.413 | 672 | 0.01 | 65 | 0.03 |

|    | RT (min) | Area ( V*sec) | % Area | Height ( V) | % Height |
|----|----------|---------------|--------|-------------|----------|
| 1  | 4.020    | 349           | 0.01   | 33          | 0.01     |
| 2  | 4.371    | 1051          | 0.02   | 86          | 0.04     |
| 3  | 6.587    | 743           | 0.01   | 98          | 0.04     |
| 4  | 7.779    | 772           | 0.01   | 74          | 0.03     |
| 5  | 8.174    | 1659          | 0.02   | 158         | 0.07     |
| 6  | 9.045    | 189           | 0.00   | 26          | 0.01     |
| 7  | 12.835   | 313           | 0.00   | 41          | 0.02     |
| 8  | 14.875   | 4859          | 0.07   | 486         | 0.20     |
| 9  | 15.369   | 6788705       | 99.65  | 238116      | 99.26    |
| 10 | 17.378   | 5265          | 0.08   | 203         | 0.08     |
| 11 | 17.977   | 6110          | 0.09   | 370         | 0.15     |
| 12 | 18.644   | 918           | 0.01   | 50          | 0.02     |
| 13 | 21.918   | 450           | 0.01   | 44          | 0.02     |
| 14 | 23.610   | 468           | 0.01   | 45          | 0.02     |
| 15 | 26.323   | 664           | 0.01   | 73          | 0.03     |

PHYSICAL STATES OF A PHARMACEUTICAL DRUG SUBSTANCE

BACKGROUND

Practically, pamoic acid salts of active pharmaceutical ingredients (APIs) have received very little attention either by pharmaceutical scientists or synthetic organic chemists. Two simplistic observations are recurring themes in the folklore (i.e. industry practice or belief) surrounding pamoic acid derivatives. In general, the preparation of a pamoate salt converts a liquid material to a solid and an improved organoleptic property has been ascribed to such salts. Organoleptic properties, for example, are smell and taste, and pamoate salts of drug substances have been suggested as eliminating the bitter taste compared with other salts (or the free base) of the drug substance. Rationally and chemically, these attributes can be assigned to pamoate salts.

It is of some historical interest that the pamoate salts of a variety of active pharmaceutical ingredients have received attention, noting that an embonate salt is identical to a pamoate salt. In the following cited literature, the pamoate was apparently chosen a) for converting a liquid active pharmaceutical ingredient into a solid, b) for eliminating the bitter taste associated with many active pharmaceutical ingredients, or c) as a process for isolating and then chemically characterizing otherwise difficult to delineate alkaloids or active pharmaceutical ingredients. For instance, U.S. Pat. No. 5,232,919 [Scheffler, et al.], the disclosure of which is totally incorporated herein by reference, discloses azelastine embonate and pharmaceutical formulations/compositions which contain it; said embonate salt to eliminate the bitter taste of azelastine alone.

Further, the French Patent 1,461,407 [Saias, et al.], the disclosure of which is totally incorporated herein by reference, discloses a process for the preparation of amine pamoates where the amine component includes piperazine, promethazine, papaverine, pholocodine, codeine, narcotine and chlorpheniramine.

The United Kingdom Patent Specification 295,656, [Carpmaels & Ransford, agents for applicants] the disclosure of which is totally incorporated herein by reference, discloses a process for the manufacture of poorly soluble salts of organic bases and alkaloids. The disclosure further indicates the process for manufacture provides sparingly soluble and tasteless salts of organic nitrogenous basic compounds including alkaloids.

U.S. Pat. No. 3,502,661 [Kasubick, et al.], the disclosure of which is totally incorporated herein by reference, discloses a process for the preparation of variously substituted pyridinium and imidazolines along with their acid addition salts. Some examples indicate pamoate salts prepared for select organic bases.

U.S. Pat. No. 2,925,417 [Elslager, et al.], the disclosure of which is totally incorporated herein by reference, discloses quinolinium salts of pamoic acid and a process for their manufacture.

Further, the following cited references indicate the incorporation of pamoate salts in pharmaceutical formulations for providing the controlled release of water insoluble polypeptides or the oil soluble azelastine. Hence, U.S. Pat. No. 5,776,885 [Orsolini, et al.], the disclosure of which is totally incorporated herein by reference, discloses a pharmaceutical composition for the sustained and controlled release of water insoluble polypeptides whereby the therapeutically active peptide is in the form of its pamoate, tannate or stearate salt.

U.S. Pat. No. 5,445,832 [Orsolini, et al.], the disclosure of which is totally incorporated herein by reference, discloses a process for the preparation of microspheres made of a biodegradable polymeric material whereby a water soluble peptide or peptide salt is converted into a corresponding water-insoluble peptide salt selected from pamoates, stearates or palmitates of the peptide.

U.S. Pat. No. 5,439,688 [Orsolini, et al.], the disclosure of which is totally incorporated herein by reference, discloses a process for preparing a pharmaceutical composition in the form of microparticles designed for the controlled release of a drug that includes a biodegradable polymer and where the active ingredient can be selected from a group of possible salts, one being a pamoate.

U.S. Pat. No. 5,271,946 [Hettche] the disclosure of which is totally incorporated herein by reference, discloses a controlled release azelastine containing pharmaceutical composition whereby azelastine is incorporated into the formulation as its pamoate or other pharmaceutically active salt.

U.S. Pat. No. 5,225,205 [Orsolini, et al.], the disclosure of which is totally incorporated herein by reference, discloses a pharmaceutical composition in the form of microparticles; the formulation consisting of a peptide as its pamoate, tannate, stearate or palmitate salt; the formulation to provide a controlled release, pharmaceutical composition for the prolonged release of a medicamentous substance.

While the patent literature describes a number of known active pharmaceutical ingredients as their pamoate salts, surprisingly the Food and Drug Administration (FDA) has only three commercial products currently approved containing the pamoate moiety. These products are hydroxyzine pamoate, imipramine pamoate and triptorelin pamoate. Clearly, the pamoate moiety is an under-represented class of pharmaceutical salts and there remains a need to further explore the benefits available from producing pamoate salts of APIs.

In their Guidance for Industry, ANDAs: Pharmaceutical Solid Polymorphism, the United States Food and Drug Administration (FDA) has focused attention on the importance of characterizing the polymorphic behavior of an Active Pharmaceutical Ingredient (API) and the impact that behavior has on the commercial presentation of a formulated drug product. Indeed, the physical and chemical properties of an API's different polymorphs often display different behavior in their intended application and are known to influence and/ or impact properties important to pharmaceutical compositions. These properties include the API's bioavailability, solubility, dissolution behavior, stability profile, permeability and manufacturing handling robustness including but not limited to uniformity of mixing, compaction in compression steps for tablet making, and the flow characteristics of the bulk blend.

The pharmaceutical industry has responded to the cited FDA Guidance and a number of patents have been allowed that provide solutions to a host of problems arising from polymorphic issues. In some cases, a given issue or problem was resolved by formulating a drug product with a specific API polymorph. In other cases, a new API polymorph was isolated and characterized to overcome prior art and/or to solve a technical issue. A few examples are representative of the substantive activity in polymorph research and development for pharmaceutical compositions.

A method for obtaining the most thermodynamically stable polymorph of formoterol tartrate and its subsequent purification by recrystallization is described in U.S. Pat. No. 6,472,563 (Tanoury, et al.), incorporated herein by reference. Tanoury et al. in U.S. Pat. No. 6,720,453, the disclosure of which is totally incorporated herein by reference, also in relation to formeterol tartrate polymorphs, describe a process for obtaining a highly pure salt of a single enantiomer of the API.

An instructive series of patents include U.S. Pat. No. 5,736,541 [Bunnell et al.], U.S. Pat. No. 6,251,895 B1 [Larsen et al.] and U.S. Pat. No. 7,022,698 B2 [Hamied et al.], the disclosure of each is totally incorporated herein by reference, and relate to the polymorphic forms of olanzapine and its use in pharmaceutical compositions. The API, olanzapine, has been isolated and characterized in several different free-base, polymorphic forms with each polymorph demonstrating a different stability profile and each subject to formulation changes suitable for use as a final dose product.

U.S. Pat. No. 5,120,850 [Bod et al.] and U.S. Pat. No. 5,128,477 [Bod et al.], the disclosure of each being totally incorporated herein by reference, relates to the selective crystallization or precipitation of two morphologically homogeneous forms of famotidine, a thiazole derivative. In U.S. Pat. No. 4,283,408 [Hirata et al.], the disclosure of which is totally incorporated herein by reference, famotidine and its pharmaceutically acceptable salts were formulated into gastric acid secretion inhibitors.

Recently, U.S. Pat. No. 6,987,111 B2 [Greco et al], the disclosure of which is totally incorporated herein by reference, discloses pharmaceutical compositions possessing long acting and/or extended release profiles incorporating the pamoate salts of aripiprazole, olanzapine and haloperidol. The inventors' observations contained in their claims purports to the physical appearance of the salt as a needle, or as crystalline, however no polymorphic examination, dissolution profile, bioavailability or pharmacokinetics was reported.

An important issue surrounding the current unprecedented activity in generic drug development is the evaluation of existing pharmaceutical products to identify their polymorphic behavior and to incorporate the correct polymorph into a generic commercial offering. Simultaneously, the generic product must exhibit a favorable impurity profile compared to the original, innovator product. Frequently for older drug products, the degree to which the active ingredient may be present in one or more polymorphic forms has not been explored or well characterized (if at all). Different polymorphic forms can radically influence a drug's solubility and result in a dramatically altered pharmacokinetic behavior for the patient.

To demonstrate the preceding assertion, U.S. Pat. No. 3,326,896 [Holstius] is illustrative, and the disclosure of which is totally incorporated herein by reference. The author discloses three embonic (pamoic acid) addition salts free from unpleasant taste and local anesthetic properties, and useful for the treatment of depression. The addition salt of 5-(3-dimethylaminopropyl)dihydro-5H-dibenz-[b,f]-azepine, (imipramine), was absorbed more slowly than the corresponding hydrochloride salt. Processes for making the embonic acid addition salts in aqueous and organic media were also disclosed. A review of the reported laboratory work reveals an anomalous observation in that the same "melting point" was reported for the pamoate salt of 5-(3-dimethylaminopropyl)-10,11-dihydro-5H-dibenz[b,f]azepine as for 5-(3-methylaminopropyl)-10,11-dihydro-5H-dibenz[b,f]azepine derivative. Both "melting points" were reported as 125-150° C. even though they are different compounds prepared under the same aqueous conditions. Melting ranges of this magnitude are generally associated with the presence of impurities and/or the presence of solvates/hydrates. In connection with the material the authors isolated, no crystalline forms were observed or claimed, and indeed, no attempt was made to characterize crystalline forms through techniques such as microscopy or X-ray powder diffraction patterns. Further, no calorimetry was performed thus clues gleaned from heats of fusion or heats of hydration were not provided. Interestingly, the author claims the embonic acid addition salt of 5-(3-dimethylaminopropyl)-10,11-dihydro-5H-dibenz[b,f] azepine, however the salt is not characterized as the 1:1 salt or as the 2:1 salt or some mixture thereof. Perhaps the broad melting point reported in the specification suggests the presence of impurities and/or the presence of unidentified solvates or hydrates.

With the existing commercial need and societal demand for generic drug products, the current invention is directed toward novel polymorphic forms of imipramine pamoate and their subsequent purification.

SUMMARY

It is an object of the invention to provide improved forms of imipramine pamoate and improved control over the morphology generated during the formation thereof.

A particular feature of the present invention is the ability to characterize imipramine pamoate morphologies and to control the ratio of defined morphologies for imipramine pamoate.

These and other advantages, as will be realized, are provided in an amorphous form of imipramine pamoate characterized by a differential scanning calorimetry (DSC) thermogram exhibiting a phase transition of about 105-113° C. and a heat of fusion of at least 0.5 joules per gram.

Yet another advantage is provided in an amorphous form of imipramine pamoate characterized by an infrared (IR) absorbance spectrum as of FIG. 6.

Yet another advantage is provided in an amorphous form of imipramine pamoate characterized by a powder X-ray diffraction (PXRD) diffraction pattern as of FIG. 1.

Yet another advantage is provided in a polymorphic form of imipramine pamoate characterized by a differential scanning calorimetry (DSC) thermogram exhibiting phase transitions at about 108-115° C. and at about 137-151° C. and having associated heats of fusion of at least 0.5 Joules per gram and 8 Joules per gram respectively.

Yet another advantage is provided in a polymorphic form of imipramine pamoate characterized by an infrared (IR) absorbance spectrum as of FIG. 7.

Yet another advantage is provided in a polymorphic form of imipramine pamoate characterized by a powder X-ray diffraction (PXRD) pattern as of FIG. 2.

Yet another advantage is provided in a polymorphic form of imipramine pamoate characterized by a differential scanning calorimetry (DSC) thermogram exhibiting a phase transition of about 160-171° C. and a heat of fusion of at least 2 Joules per gram.

Yet another advantage is provided in a polymorphic form of imipramine pamoate characterized by an infrared (IR) absorbance spectrum as of FIG. 3.

Yet another advantage is provided in a polymorphic form of imipramine pamoate characterized by a powder X-ray diffraction (PXRD) pattern as of FIG. 3.

Yet another advantage is provided in a polymorphic form of imipramine pamoate characterized by a differential scanning calorimetry (DSC) thermogram exhibiting a phase transition at about 140-160° C. heat of fusion of at least 18 Joules per gram.

Yet another advantage is provided in a polymorphic form of imipramine pamoate characterized by an infrared (IR) absorbance spectrum as of FIG. 9.

Yet another advantage is provided in a polymorphic form of imipramine pamoate characterized by a powder X-ray diffraction (PXRD) pattern as of FIG. 4.

Yet another advantage is provided in a polymorphic blend of imipramine pamoate Form I and imipramine pamoate Form III characterized by a differential scanning calorimetry (DSC) thermogram exhibiting phase transitions of about 60-110° C. and at about 150-170° C. and each possessing a heat of fusion is at least 10 Joules per gram.

Yet another advantage is provided in a polymorphic blend of imipramine pamoate Form I and imipramine pamoate Form III characterized by an infrared (IR) absorbance spectrum as of FIG. 10.

Yet another advantage is provided in a polymorphic blend of imipramine pamoate Form I and imipramine pamoate Form III characterized by a powder X-ray diffraction (PXRD) pattern as of FIG. 5.

Yet another advantage is provided in a process for preparing purified forms of imipramine pamoate comprising the steps:

a) combining the pH adjusted solutions of imipramine hydrochloride and disodium pamoate at a metered or unmetered rate of combination, b) adding an organic solvent to the reaction mixture during the reagent combining step or afterward, c) warming the reaction solution to a temperature less than or equal to the added solvent's azeotropic boiling point, d) cooling and precipitating solids from the reaction mixture e) collecting the precipitated solids by filtration or centrifugation, f) optionally washing the collected solids with water, solvent or a mixture thereof, g) drying the solids, optionally under vacuum at temperatures sufficient to remove the water and solvent, and h) assessing the quality of the dried solid by chromatographic methods.

Yet another advantage is provided in a blend of at least one imipramine pamoate polymorphic form with another form.

Yet another advantage is provided in a process for preparing a mixture of polymorphic forms of imipramine pamoate comprising the steps of a) a process temperature change during the reaction between imipramine as its mineral acid salt with a solution of pamoic acid or its salt such that the temperature of reaction providing a lower melting point form is increased to the temperature range which provide at least one second, higher melting polymorph, and b) the addition of a secondary solvent capable of allowing the reaction temperature to increase to that temperature where at least one additional polymorph is formed, and c) a process temperature change during drying of the isolated solids for the reaction mixture such that the temperature is increased for a time period required to produce at least one additional polymorph, Yet another advantage is provided in a process for preparing a mixture of polymorphic forms of imipramine pamoate comprising the steps of:

a) preparing the individual forms to be blended selected from the group defined as Form I, Form II, Form III, Form IV, Form V and Form VI.

b) combining the desired forms of imipramine pamoate in a pre-determined weight ratio of each component in a common vessel, c) mixing, blending, tumbling, rotating, or by other mechanical action to insure and assure homogenous intermixing of the two forms, and d) assessing the quality of the polymorphic blend by analytical methodology selected from differential scanning calorimetry (DSC), Infrared absorption (IR), powder x-ray diffraction (PXRD) and chromatographic methodology.

Yet another advantage is provided in a polymorphic form of imipramine pamoate characterized by a differential scanning calorimetry (DSC) thermogram exhibiting phase transitions at about 98-118° C. and at about 128-145° C. and having associated heats of fusion of at least 50 and 8 Joules per gram, respectively, Yet another advantage is provided in a polymorphic form of imipramine pamoate characterized by an infrared (IR) absorbance spectrum consistent with and generally comparable to that represented by FIG. 19.

Yet another advantage is provided in a polymorphic form of imipramine pamoate characterized by a powder X-ray diffraction (PXRD) pattern consistent with and generally comparable to that represented in FIG. 18.

Yet another advantage is provided in a synthetic process capable of producing multiple polymorphic forms of imipramine pamoate comprising at least one step selected from isolating amorphous imipramine pamoate from the reaction vessel; isolating amorphous imipramine pamoate in combination with a selected polymorphic form of imipramine pamoate; isolating a single polymorphic form of imipramine pamoate and isolating a mixture of polymorphic forms of imipramine pamoate.

Yet another advantage is provided in a synthetic process capable of inter-converting physical forms of imipramine pamoate comprising at least one step selected from subjecting amorphous imipramine pamoate to solvent and temperature conditions sufficient for generating an amount of polymorphic imipramine pamoate from 1-100% of the single polymorph; subjecting an imipramine pamoate polymorph exhibiting a lower phase transition temperature to solvent and temperature conditions sufficient for generating an amount of a second polymorphic form of imipramine pamoate from 1-100% and said second polymorphic form having a higher phase transition temperature and subjecting a mixture of amorphous imipramine pamoate and an imipramine pamoate polymorph exhibiting a lower phase transition temperature to solvent and temperature conditions sufficient for generating an amount of a second polymorphic imipramine pamoate from 1-100%, and said second polymorphic form having a higher phase transition temperature.

Yet another advantage is provided in a pharmaceutical composition of at least one polymorphic form of imipramine pamoate suitable for use in treating depression, fibromyalgia, childhood nocturnal enuresis and adult urinary incontinence, trichotillomania, post-traumatic stress disorder, panic disorder and to provide analgesic-like relief for neuropathic pain.

Yet another advantage is provided in a pharmaceutical composition comprising a polymorphic form of imipramine pamoate comprising at least one material selected from the group consisting of imipramine pamoate Form I, imipramine pamoate Form II, imipramine pamoate Form III, imipramine pamoate Form IV, imipramine pamoate Form V and imipramine pamoate Form VI adapted for use in treating depression, fibromyalgia, childhood nocturnal enuresis and adult urinary incontinence, trichotillomania, post-traumatic stress disorder, panic disorder and to provide analgesic-like relief for neuropathic pain.

Yet another advantage is provided in a pharmaceutical composition comprising 1 to 95% amorphous imipramine pamoate and 5-99 wt % of at least one material selected from imipramine pamoate Form II, imipramine pamoate Form III, imipramine pamoate Form IV, imipramine pamoate Form V and imipramine pamoate Form VI.

Yet another advantage is provided in a process capable of inter-converting physical forms of imipramine pamoate at least one step selected from optionally subjecting amorphous imipramine pamoate to solvent and temperature conditions sufficient for generating an amount of polymorphic imipramine pamoate from 1-100% of the single polymorph; optionally subjecting an imipramine pamoate polymorph exhibiting a lower phase transition temperature to temperature conditions sufficient for generating an amount of a second polymorphic form of imipramine pamoate from 1-100% and said second polymorphic form having a higher phase transition temperature; optionally subjecting a mixture of amorphous imipramine pamoate and an imipramine pamoate polymorph exhibiting a lower phase transition temperature to temperature conditions sufficient for generating an amount of a second polymorphic imipramine pamoate from 1-100%, and said second polymorphic form having a higher phase transition temperature and optionally subjecting a mixture of amorphous imipramine pamoate and an imipramine pamoate polymorph to temperature condition sufficient for substantially converting the amorphous imipramine pamoate to the said imipramine pamoate polymorph.

Yet another advantage is provided in a pharmaceutical composition comprising:

0-100 wt % of imipramine pamoate with a phase transition of 105-133° C. and a heat of fusion of at least 0.5 joules per gram;

0-100 wt % of imipramine pamoate with a phase transition of 108-115° C. with a heat of fusion of at least 0.5 joules per gram and a phase transition of 137-151° C. with a heat of fusion of at least 8 joules per gram;

0-100 wt % of imipramine pamoate with a phase transition of 160-171° C. and a heat of fusion of at least 2 joules per gram;

0-100 wt % of imipramine pamoate with a phase transition of 140-160° C. and a heat of fusion of at least 18 joules per gram;

0-100 wt % of imipramine pamoate with a phase transition of about 60-110° C. with a heat of fusion of at least 15 joules per gram and a phase transition of about 150-170° C. with a heat of fusion of at least 15 joules per gram; and 0-100 wt % of imipramine pamoate with a phase transition of about 98-118° C. with a heat of fusion of at least 30 joules per gram and a phase transition of about 128-145° C. with a heat of fusion of at least 5 joules per gram.

DETAILED DESCRIPTION

The invention described herein and supported by the accompanying EXAMPLES and FIGURES discloses novel, polymorphic forms (including amorphous and blended forms) of imipramine pamoate and their utility in pharmaceutical compositions. The invention also describes a means to provide highly purified forms of these polymorphs and stable mixtures having at least one polymorph in combination with amorphous material.

Figure 16:
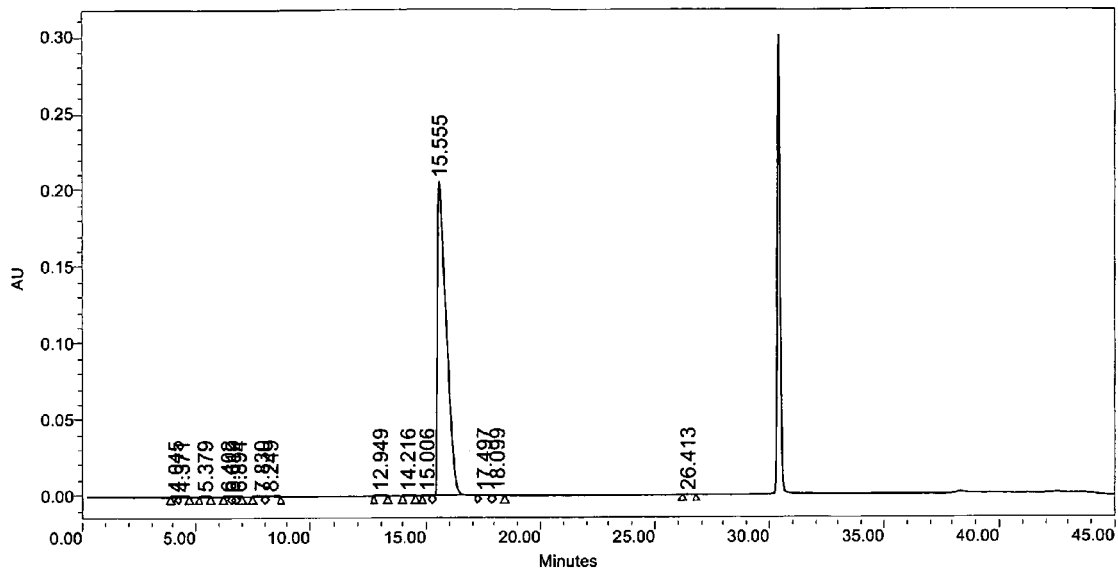
FIG. 16 is a high performance liquid chromatography chromatograph of an embodiment of the present invention.
Figure 17:
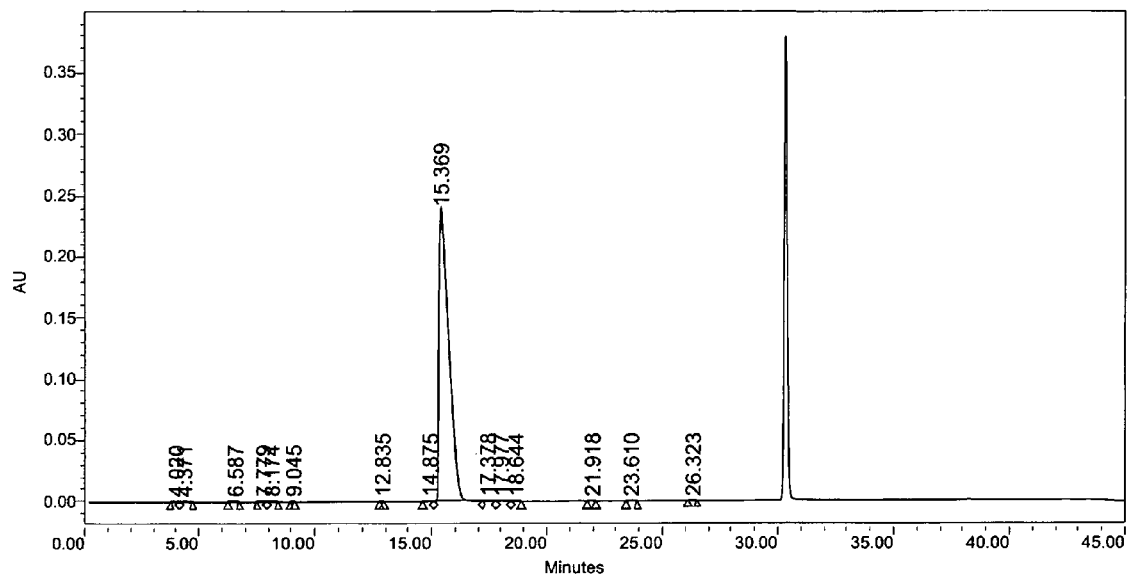
FIG. 17 is a high performance liquid chromatography chromatograph of another embodiment of the present invention.

FIGS. 1 through 5, and FIG. 18 are the diffractograms obtained from powder X-ray diffraction (PXRD) analysis of polymorphic forms, (or blends) described as Form I, Form II (a mixture containing amorphous material), Form III, Form IV, Form V (a physical mixture containing at least two forms), and Form VI (a process mixture containing at least two forms), respectively. An analytical difference characterizes each diffractogram and allows for the identification of each polymorph. In the diffractograms minor impurities of sodium chloride are indicated by peaks at about 32, 45, 57 and 66 degrees 2-theta. These are considered to be non-consequential impurities and of no significance in the material. The presence, or absence, of these peaks does not alter the interpretation or comparison of the underlying diffractogram which is to be evaluated exclusive of those peaks for the purposes of the present invention. Similarly, FIGS. 6 through 10, and FIG. 19 are the infrared spectrums obtained by Fourier Transform Infra Red (FTIR) spectrophotometry of the preceding polymorphs, respectively. It is worthy of note that FTIR is often used to distinguish polymorphs, however these spectra do not exhibit substantial variation for conclusive polymorph diagnosis. Indeed, this phenomenon may have led to the multitude of polymorphic characteristics of imipramine pamoate being previously unobserved. For additional confirmation of polymorphic identity and content, thermograms were obtained for each polymorphic form using differential scanning calorimetry (DSC). FIGS. 11 through 15, and FIG. 20 are the thermograms of the identified polymorphic forms, Form I through VI, respectively. FIG. 16 is the HPLC chromatogram of an embodiment of Form II typically employing an aqueous preparation process. In contrast, FIG. 17 is the HPLC chromatogram of a purified imipramine pamoate prepared by employing a mixed solvent system of water and an organic solvent. FIG. 21 is the differential scanning calorimetry thermogram of an embodiment of imipramine pamoate subjected to an annealing process.

Figure 2:
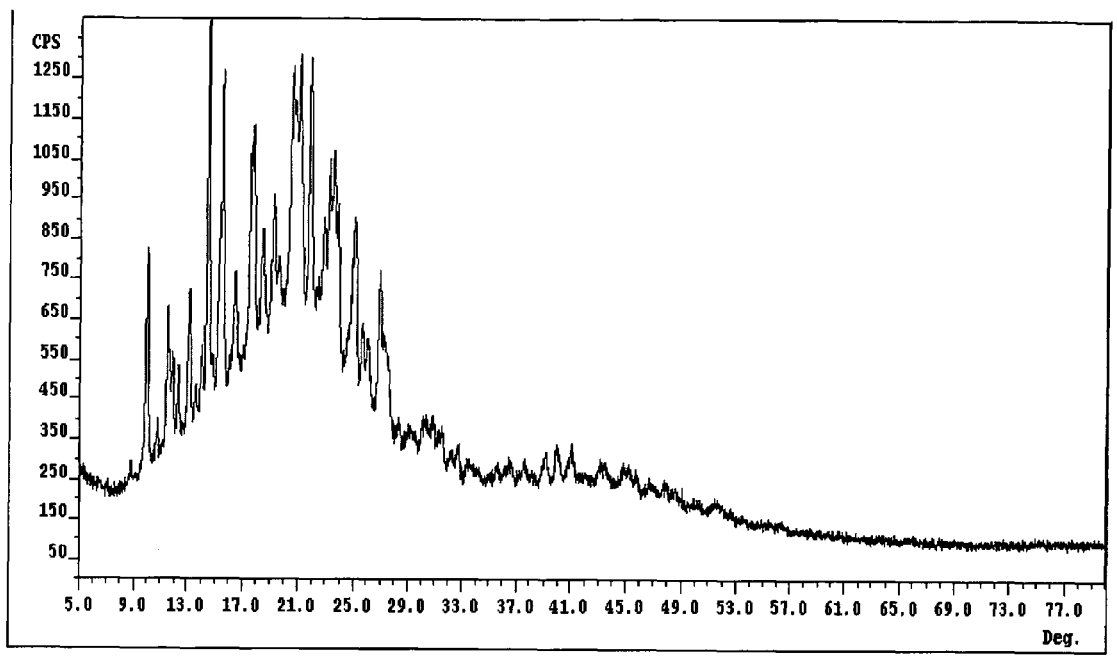
FIG. 2 is an x-ray diffraction pattern of imipramine pamoate Form II.
Figure 7:
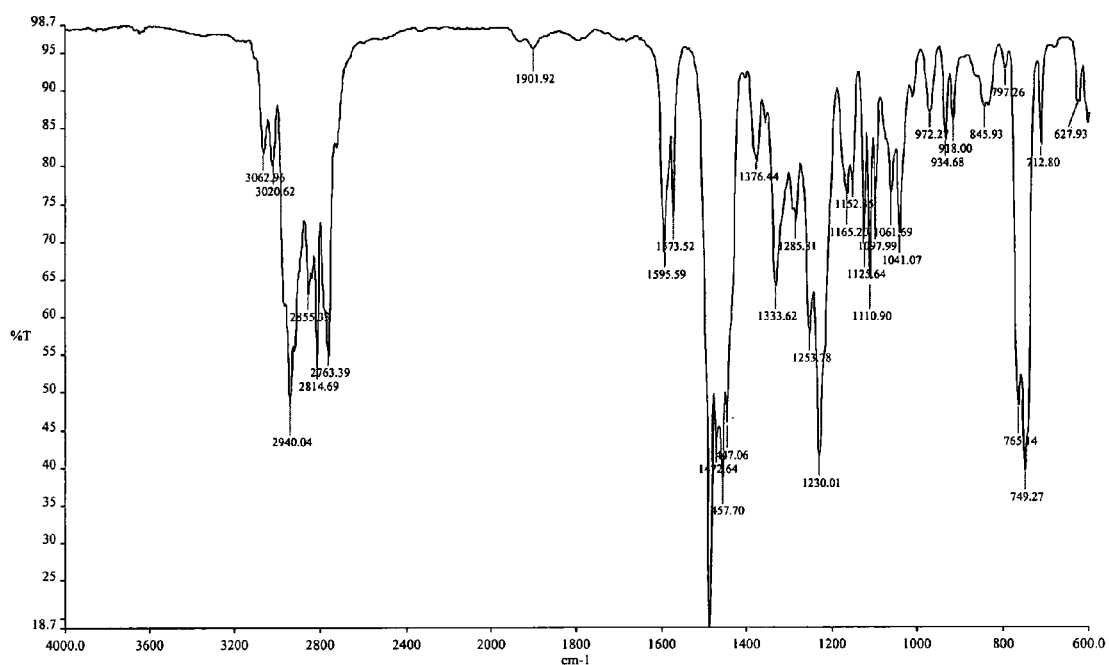
FIG. 7 is a Fourier Transform Infrared spectrum of imipramine pamoate Form II.
Figure 12:
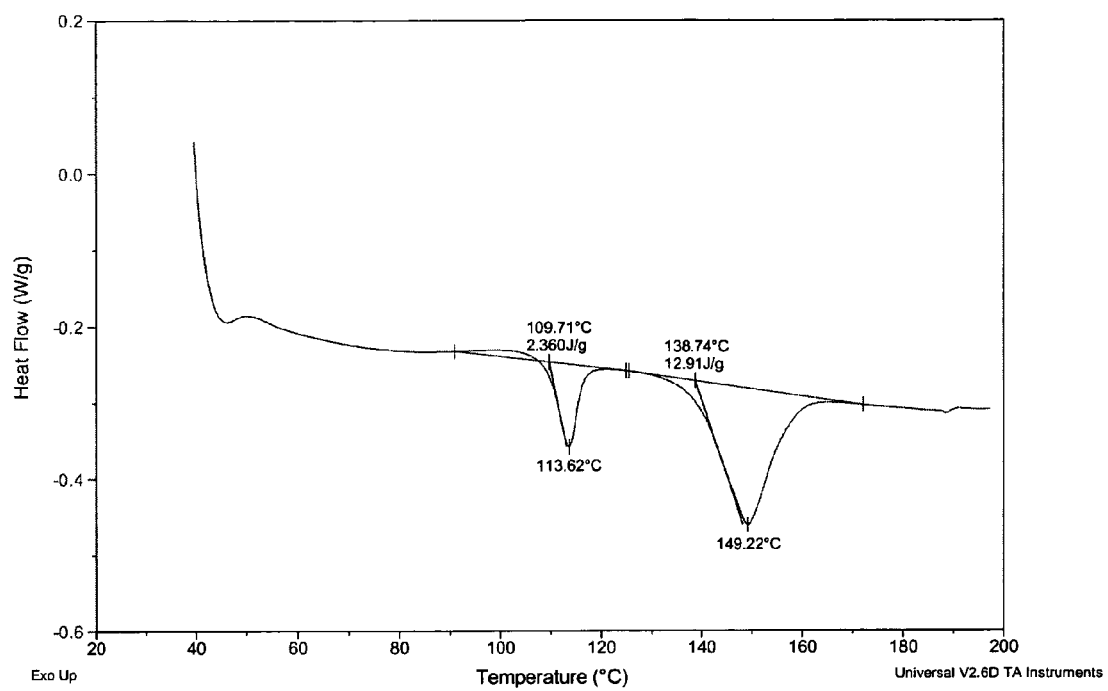
FIG. 12 is a differential scanning calorimetry thermogram of another embodiment of imipramine pamoate Form II.

Beyond the identification of the various polymorphs available to imipramine pamoate, another feature of the invention is the ability to form stable mixtures of at least one polymorph with amorphous imipramine pamoate. It is well known and recognized that amorphous forms of active ingredients have faster dissolution rates than polymorphic forms. A blended presentation of amorphous and at least one polymorphic form is represented in FIGS. 2, 7, and 12, for the PXRD diffractogram, FTIR spectrum and DSC thermogram, respectively.

Yet another important feature of this invention is the ability to produce stable blends of the polymorphic and amorphous forms. Optionally, the synthetic process can be adjusted to produce polymorphic and/or amorphous mixtures, or a physical blending of individually produced polymorphic forms, said blends optionally containing amorphous content, can be prepared. To further elucidate this comparison, Form VI is obtained by a synthetic process which concomitantly produces amorphous material and a single polymorph exhibiting a phase change (by DSC) nominally occurring around 130° C. In contrast, Form V is a physical admixture of Forms I and III.

Associated with the ability of the synthetic process to produce a mixture of amorphous and polymorphic forms is the unusual discovery of isolating and characterizing meta-stable forms of imipramine pamoate from the reaction vessel. More specifically, the selection of the reaction time and/or the reaction temperature provides a mechanism to obtain otherwise elusive polymorphs. It was generally observed that meta-stable forms (excluding the amorphous form) were obtained at the lower processing temperatures. However, the fact that stable blends of amorphous and polymorphic forms were observed across a broad temperature range (sufficient for isolation and characterization) indicates imipramine pamoate exhibits several thermodynamic "wells". Consequently, the use of the term meta-stable to describe these forms is more relevant to the processing conditions than to their use in practical dosage applications where the temperature ranges generally do not exceed 50° C.

Yet another feature of the invention is the ability to provide substantially pure amorphous and/or polymorphic forms of imipramine pamoate. In addition to the preceding purification process and in contrast to traditional recrystallization techniques, an analogous solid state "recrystallization" technique was achieved by an annealing process. It is a feature of the present invention that an imipramine pamoate salt when subjected to an annealing process and optionally in the absence of solvent induces an enhancement of polymorph purity. Upon heating a mixture of an imipramine pamoate polymorph having amorphous content, enrichment of the polymorph was observed. This observation allows for the fine-tuning of polymorph selection in the manufacturing process which optionally may include the steps of solvent/anti-solvent methodology for removal of (synthesis) impurities or polymorph enrichment followed by solids isolation and drying under annealing conditions to yield polymorph enrichment. Similarly, polymorphic transitions can be induced in compositions containing substantially one polymorph by employing an annealing process. For practical application, the annealing step can optionally occur during the manufacturing process where 1) the reaction medium of at least one solvent is simultaneously removed during drying and annealing, or 2) applying the annealing process to previously isolated and dried material. Often, recrystallization techniques are used to purify pharmaceutically useful solids, however, the essentially insoluble nature of imipramine pamoate prevents this approach to purification. Additionally, polymorph integrity is severely challenged when a given (crude) polymorph is exposed to heat and solvent during a recrystallization process. During the exploration to prepare imipramine pamoate polymorphs, high pressure liquid chromatography (HPLC) was employed to monitor the extent of preparative reactions. Similarly, in an attempt to prepare a hydrate, solvate and/or a clathrate form of imipramine pamoate, relatively crude material was exposed to a solvent-saturated environment. Both chromatographic monitoring of reaction conditions and visual analysis of the solvent exposures indicated impurities could be removed under specialized conditions despite the nearly universally insoluble nature of imipramine pamoate in a variety of solvent systems. In an analytical comparison of preparative synthetic techniques, the present invention resulted in achieving essentially pure imipramine pamoate as evidenced by the HPLC chromatograms shown in FIGS. 16 and 17. FIG. 16 reflects the analysis of the aqueous process typically employed to prepare pamoates. FIG. 17 is indicative of a process employing a mixed solvent system of water and an organic solvent. For practical purposes, the organic solvent was selected from those having miscibility with water (for example ethanol or ethyl acetate). However, the invention is not limited or restricted by miscibility of the organic solvent with water and to the extent purification is accomplished, the organic solvent selection can have anti-solvent properties.

In addition to the preceding purification process and in contrast to traditional recrystallization techniques, an analogous solid state "recrystallization" technique was achieved by an annealing process. It is a feature of the present invention that an imipramine pamoate salt when subjected to an annealing process and optionally in the absence of solvent induces an enhancement of polymorph purity. Upon heating a mixture of an imipramine pamoate polymorph having amorphous content, enrichment of the polymorph was observed. This observation allows for the fine-tuning of polymorph selection in the manufacturing process which optionally may include the steps of solvent/anti-solvent methodology for removal of (synthesis) impurities followed by solids isolation and drying under annealing conditions to yield polymorph enrichment. Similarly, polymorphic transitions can be induced in compositions containing substantially one polymorph by employing an annealing process. For practical application, the annealing step can optionally occur during the manufacturing process where 1) the reaction medium of at least one solvent is simultaneously removed during drying and annealing, or 2) applying the annealing process to previously isolated and dried material.

The discovery of the annealing process provided some insight into the multitude of polymorphs obtained from the different experimental conditions employed. A trend analysis was performed by comparing each reaction condition (reagent addition rate, reaction temperature, hold time, isolation temperature, solvent effect and drying conditions) with the analytical data characterizing the isolated product. The analysis suggests that increasing the organic solvent content of the reaction mixture leads to a higher phase transition temperature observed in the isolated polymorph when the reaction temperature was elevated. The reaction hold times and drying conditions do not seem to impact the formation of the polymorphs characterized by a higher temperature transition (DSC).

In aqueous systems, the reaction temperature, hold times and drying conditions are significant factors in determining the polymorph obtained. By way of example, amorphous material is obtained under aqueous conditions with a short hold time. However, as the reaction hold time is extended, amorphous material is converted to an analytically recognizable polymorph. If the reaction conditions are maintained (with the exception of lowering the reaction temperature), amorphous material is generated along with a lower temperature phase transition polymorph that was originally absent.

The trend observed can be summarized as higher reaction temperatures yield a higher phase transition polymorph. This observation is consistent with the previously described annealing process, and indicates a thermodynamic and kinetic momentum leading to a stable, high phase transition temperature polymorph. The situation becomes more complex as the solvent polarity of the reaction mixture is altered. However, here too, temperature seems to be the dominating factor such that the presence of a non-polar co-solvent employed at lower reaction temperature provides polymorphs with lower temperature phase transitions. And, as discussed above, the lower phase transition polymorphs (or amorphous material) can be converted to a higher phase transition temperature polymorph by an annealing process.

Interestingly, tricyclic antidepressants and imipramine in the specific, exhibit therapeutic benefit besides the treatment of depression. Imipramine has been used in the treatment of fibromyalgia, childhood nocturnal enuresis and other types of urinary incontinence, trichotillomania, post-traumatic stress disorder, panic disorder and to provide analgesic-like relief for neuropathic pain. Kravitz et al., in the Journal of Rheumatology, has reported a relationship between imipramine binding, serotonin uptake and the link between fibromyalgia and depression. An overview of the medical treatments for fibromyalgia is well documented on the University of Maryland Medical Center's website, www.umm.edu/patiented/articles.

Jorgensen et al., in clinical Pharmacokinetics, has reported the clinical effects of imipramine treatment of childhood enuresis. Similarly, Lake et al reports in clinical Pharmacology and Therapeutics the effects of imipramine in enuretic boys. Imipramine has also been reported in a review article found in Modern Drug Discovery for the treatment of urge incontinence particularly in adult females.

A less recognized, or perhaps under-reported condition, is the use of imipramine in treating trichotillomania (chronic hair pulling). In Clinician Review, Whitaker et al. reports the use of tricyclic antidepressants for the treatment of this behavior. Further, Weller et al. reported in the Journal of the American Academy of Child Adolescence Psychiatry the successful treatment of a prepubertal child with imipramine for trichotillomania and a major depressive disorder.

In contrast to trichotillomania, posttraumatic stress disorder (PTSD) has become a common and frequent diagnosis by mental health professionals caring for the victims of hurricanes, terrorist attacks and those people involved in disturbing events occurring in our society and in the world. Kosten et al. report in the Journal of Nerve and Mental Disorders, the use of phenelzine or imipramine in the treatment of PTSD.

Rynn et al., in the Journal of Clinical Psychopharmacology, report the use of imipramine and buspirone in patients with panic disorder and who are discontinuing therapy employing benzodiazepines. Anxiety and depression symptoms were reduced and facilitated the taper process from benzodiazepine therapy.

Enggaard et al. report in Pain, the analgesic effect of codeine as compared to imipramine in different human experimental pain models. Similarly, Rasmussen et al. report in Therapuetic Drug Monitoring the therapeutic drug monitoring-based imipramine treatment in neuropathic pain.

The preceding therapeutic indications and treatments ascribed to imipramine are applications for the imipramine pamoate polymorphic inventions described herein. The development of imipramine pamoate pharmaceutical compositions are enabled by the novel discovery of these additional presentations of imipramine as pamoate polymorphs, amorphous material, and various combinations of the polymorphic forms with and without an amorphous component.

The following Experimental descriptions and Examples are illustrative of how to practice the invention.

EXPERIMENTAL

Samples were evaluated using a Differential Scanning Calorimeter from TA Instruments (DSC 2010). Prior to analysis of samples, a single-point calibration of the TA Instruments DSC 2010 Differential Scanning Calorimeter (DSC 2010) with the element indium as calibration standard (156.6±0.25° C.) was completed.

IR Spectra were obtained in a KBr disc using a Perkin Elmer Spectrum BX Fourier Transform Infrared Spectrophotometer. Instrument calibration was performed using a NIST traceable polystyrene standard. Spectra were obtained over the frequency range of 4000 to 600 cm$^{-1}$ with 32 scans per minute, 4 cm$^{-1}$ resolution at 2 cm$^{-1}$ intervals. For the purposes of demonstrating the present invention infrared spectra are formed by mixing the sample with potassium bromide. The pamoate (~8-12 mg/~8-14% wt/wt) was loaded to dry KBr (~100-120 mg) then mixed (mortar/pestle). A portion of this mixture was compressed in a die by employing a minimum amount of pressure to form a thin, and suitably transparent disc. A blank KBr disc was also prepared and its spectrum subtracted from that of the sample pamoate.

Powder X-Ray diffraction patterns were acquired on a Scintag XDS2000 powder diffractometer using a copper source and a germanium detector.

HPLC analyses were performed on a Waters 1525 Binary HPLC Pump chromatograph using a Waters 2487 Dual A Absorbance Detector.

Imipramine Pamoate

The pamoate salt of Imipramine can be prepared by treatment of Imipramine with pamoic salt or pamoic acid in a solvent or solvent mix. Imipramine pamoate was prepared by adding a solution of imipramine in an appropriate solvent, e.g. acidic water, to a solution of disodium pamoate, pamoic acid or other pamoate salt and stirred resulting in precipitation of the salt.

For the purposes of the present invention the forms of imipramine pamoate will be designated as imipramine pamoate (Form I) through imipramine pamoate (Form VI) with the forms defined as provided herein.

Figure 1:
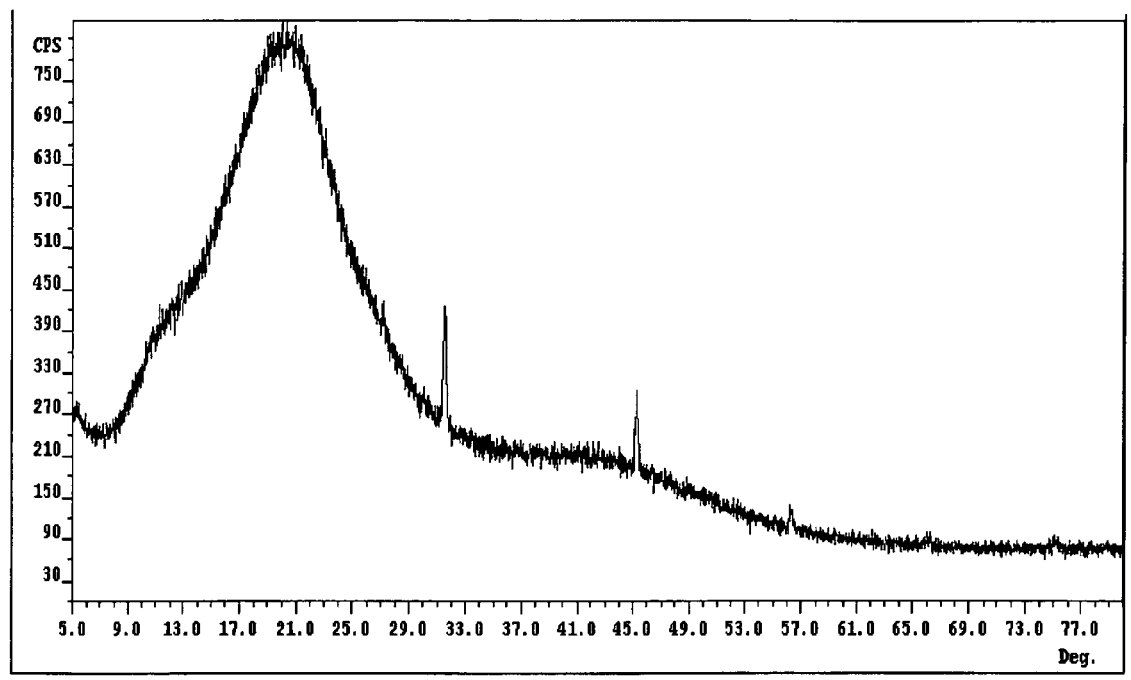
FIG. 1 is an x-ray diffraction pattern of imipramine pamoate Form I.
Figure 6:
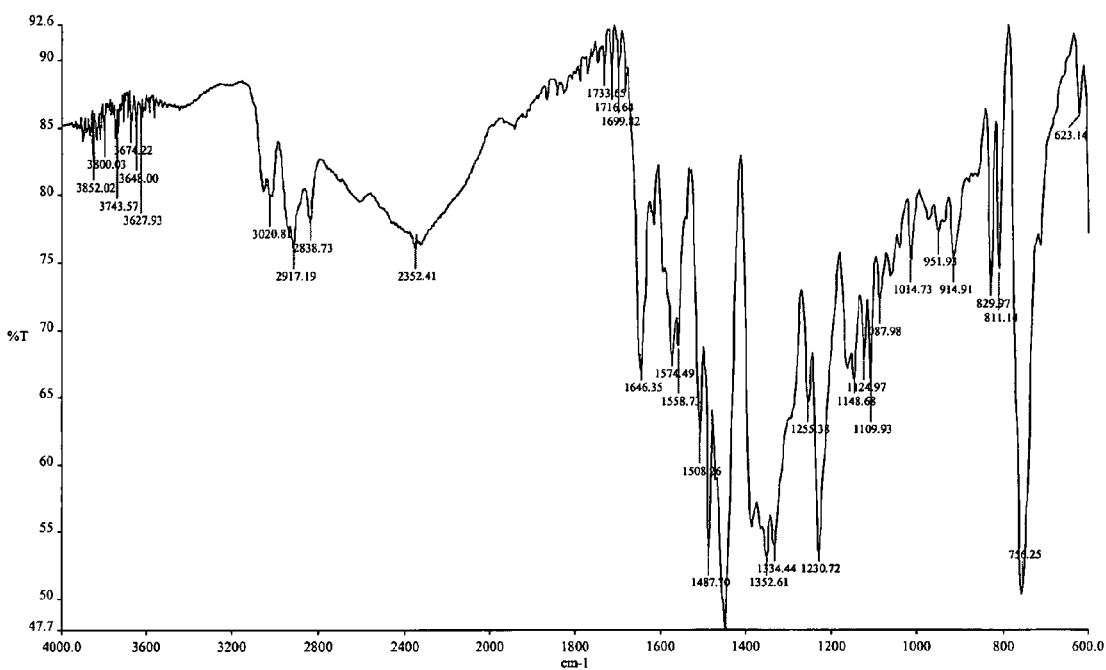
FIG. 6 is a Fourier Transform Infrared spectrum of imipramine pamoate Form I.
Figure 11:
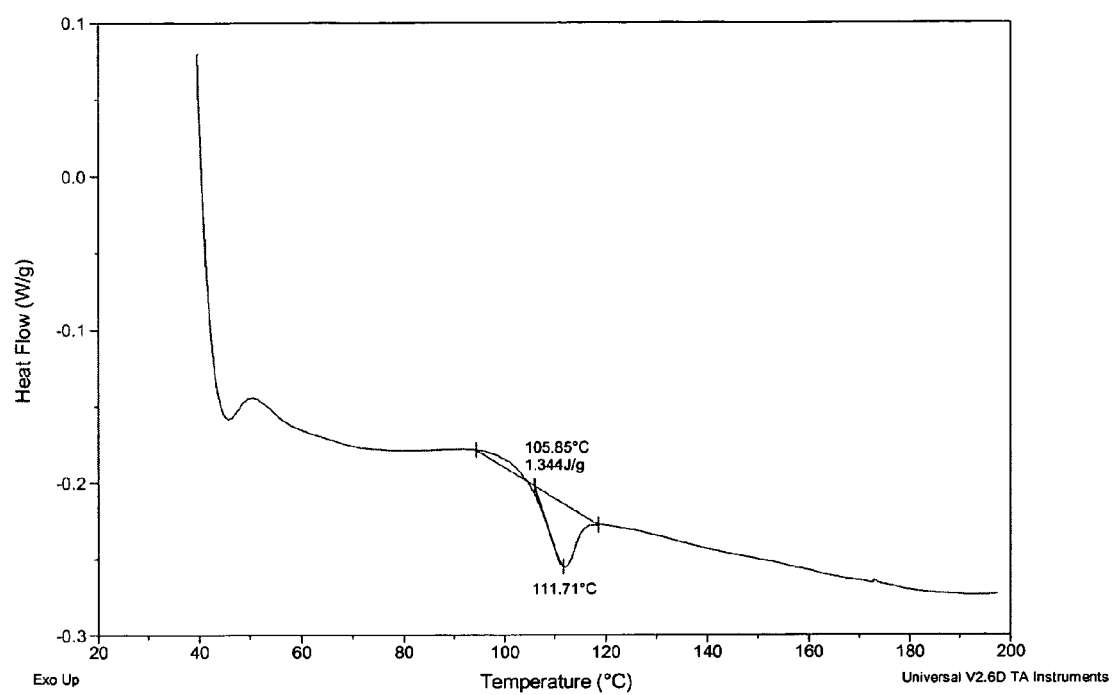
FIG. 11 is a differential scanning calorimetry thermogram of an embodiment of imipramine pamoate Form I.

Imipramine pamoate Form I is defined as having at least one characteristic, more preferably at least two characteristics selected from:

a) a phase transition as determined by DSC of 105-113° C. preferably with a heat of fusion of at least 0.5 Joules per gram and more preferably 1-2 joules per gram;

b) an x-ray diffraction pattern as of FIG. 1;

c) an infrared spectrum as of FIG. 6, d) a thermogram as measured by differential scanning calorimetry as of FIG. 11; and e) prepared by the process comprising the steps of:
   i) combining the pH adjusted solutions of imipramine hydrochloride with disodium pamoate,
   ii) warming the solution to about 53° C. for about 1-2 hours,
   iii) cooling and precipitating solids from the reaction solution at a temperature less than 20° C.,
   iv) collecting the precipitated solids by filtration or centriguation,
   v) washing the collected solids, and
   vi) drying the solids.

In one embodiment the Imipramine pamoate Form I is prepared by the steps consisting of:
   i) combining the pH adjusted solutions of imipramine hydrochloride with disodium pamoate,
   ii) warming the solution to about 53° C. for about 1-2 hours,
   iii) cooling and precipitating solids from the reaction solution at a temperature less than 20° C., and
   iv) isolating and purifying the sample.

Imipramine pamoate Form II is defined as having at least one characteristic, more preferably at least two characteristics selected from:

a) phase transitions as determined by DSC of 108-115° C. and 137-151° C.;

b) an x-ray diffraction pattern as of FIG. 2;

c) an infrared spectrum as of FIG. 7, d) a thermogram as measured by differential scanning calorimetry as of FIG. 12 exhibiting phase transitions at about 108-115° C. and at about 137-151° C. and having associated heats of fusion of at least 0.5 and 8 Joules per gram respectively; and e) prepared by the process comprising the steps of:
   i) adding the pH adjusted solution of imipramine hydrochloride in a gradual, metered manner to the pH adjusted solution of disodium pamoate,
   ii) warming the reaction solution to about 55° C. until the polymorphic form appears,
   iii) cooling and precipitating solids from the reaction mixture at a temperature less than 25° C.,
   iv) collecting the precipitated solids by filtration or centrifugation,
   v) washing the collected solids, and
   vi) drying the solids.

Figure 3:
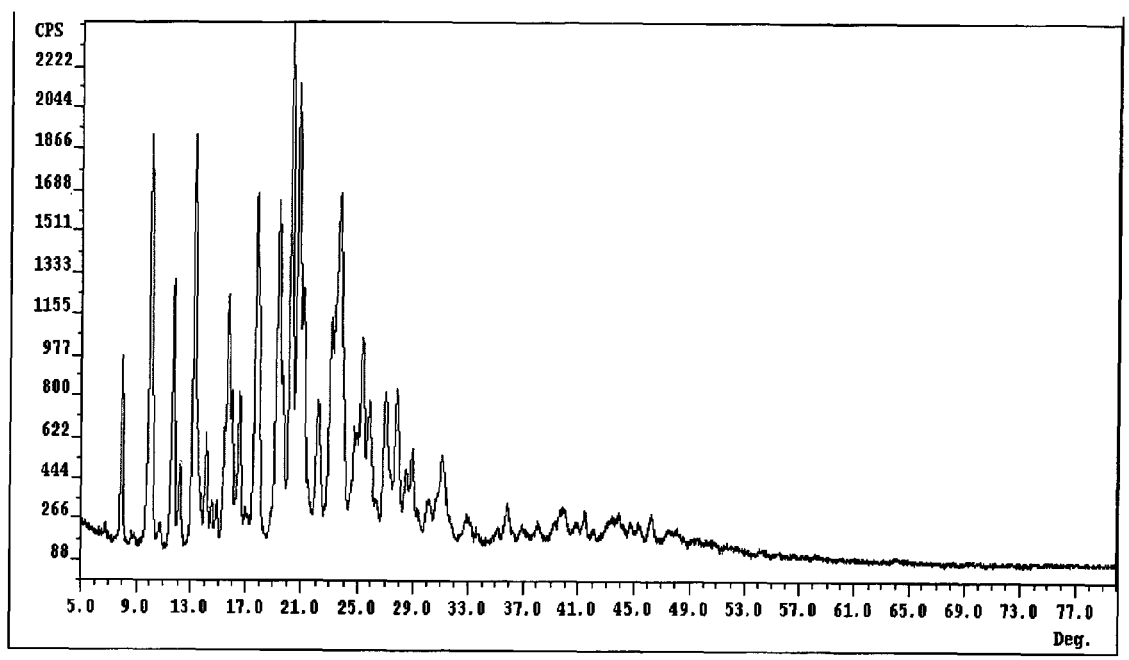
FIG. 3 is an x-ray diffraction pattern of imipramine pamoate Form III.
Figure 8:
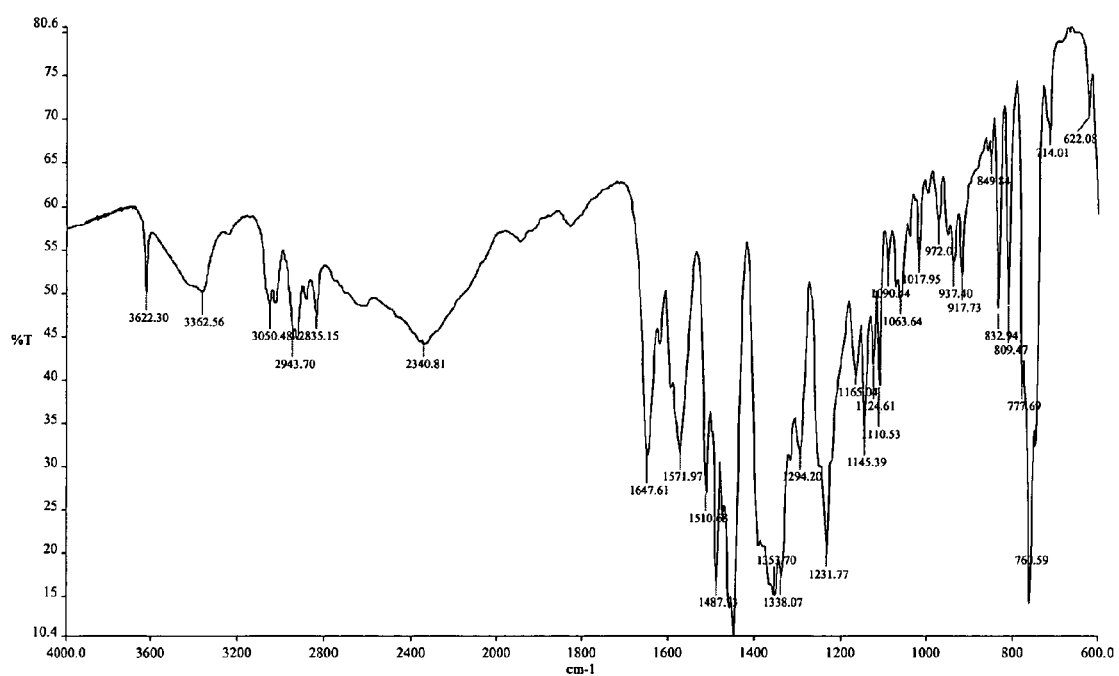
FIG. 8 is a Fourier Transform Infrared spectrum of imipramine pamoate Form III.
Figure 13:
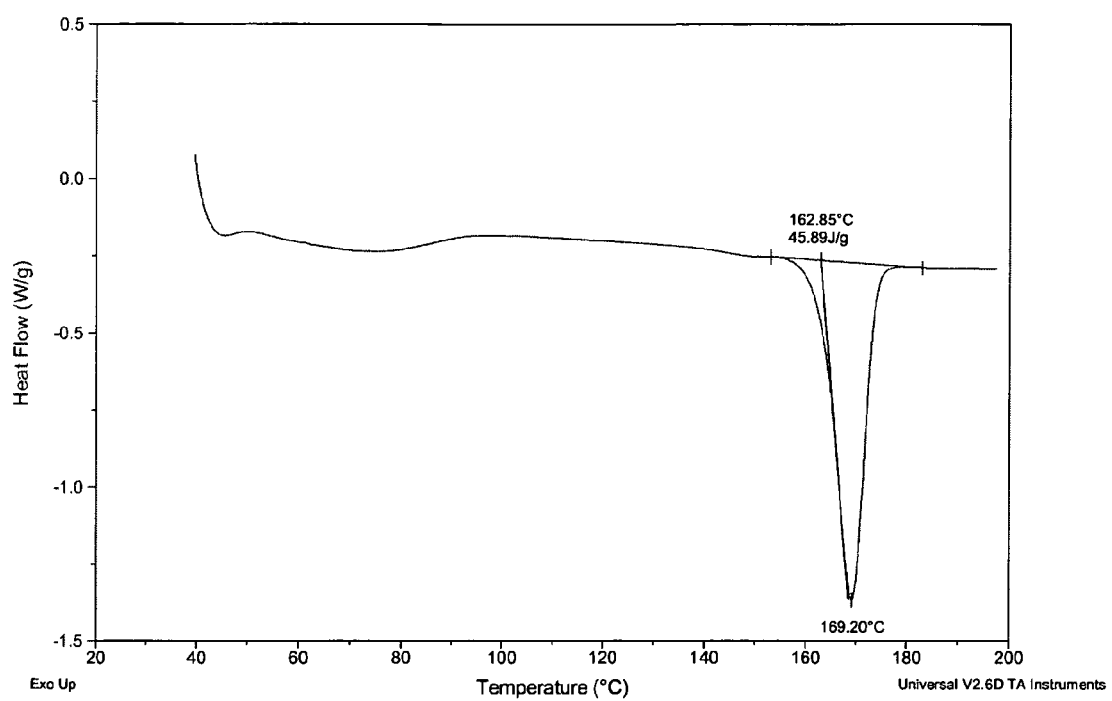
FIG. 13 is a differential scanning calorimetry thermogram of imipramine pamoate Form III.

In one embodiment the Imipramine pamoate Form II is prepared by the process consisting of the steps of:
   i) adding the pH adjusted solution of imipramine hydrochloride in a gradual, metered manner to the pH adjusted solution of disodium pamoate,
   ii) warming the reaction solution to about 55° C. until the polymorphic form appears,
   iii) cooling and precipitating solids from the reaction mixture at a temperature less than 25° C.,
   iv) isolating and purifying the sample, and
   v) drying the solids under vacuum at about 88-97° C. for 7-12 hours Imipramine pamoate Form III is defined as having at least one characteristic, more preferably at least two characteristics selected from:

a) a phase transition as determined by DSC of 160-171° C.;

b) an x-ray diffraction pattern as of FIG. 3;

c) an infrared spectrum as of FIG. 8, d) a thermogram as measured by differential scanning calorimetry as of FIG. 13 exhibiting a phase transition at about 160-171° C. with a heat of fusion of at least 2 Joules per gram and more preferably 35-55 Joules per gram; and e) prepared by the process of:
   i) combining imipramine pamoate Form II with a solvent or combination of solvents selected from water and short chain alcohols,
   ii) warming the mixture to about 76° C. until the polymorphic form appears
   iii) cooling and precipitating solids from the reaction mixture at a temperature less than 25° C.,
   iv) collecting the precipitated solids by filtration or centrifugation,
   v) washing the collected solids with water, and
   vi) drying the solids under vacuum at about 103° C. for a sufficient time to provide dry solid.

In one embodiment Imipramine pamoate Form III is prepared by the process consisting of the steps:
   i) combining imipramine pamoate Form II with a solvent or combination of solvents selected from water and short chain alcohols,
   ii) warming the reaction solution to about 76° C. until the polymorphic form appears
   iii) cooling and precipitating solids from the reaction mixture at a temperature less than 25° C.,
   iv) isolating and purifying the sample, and
   v) drying the solids under vacuum at about 99-107° C. for at least 12 hours.

Figure 4:
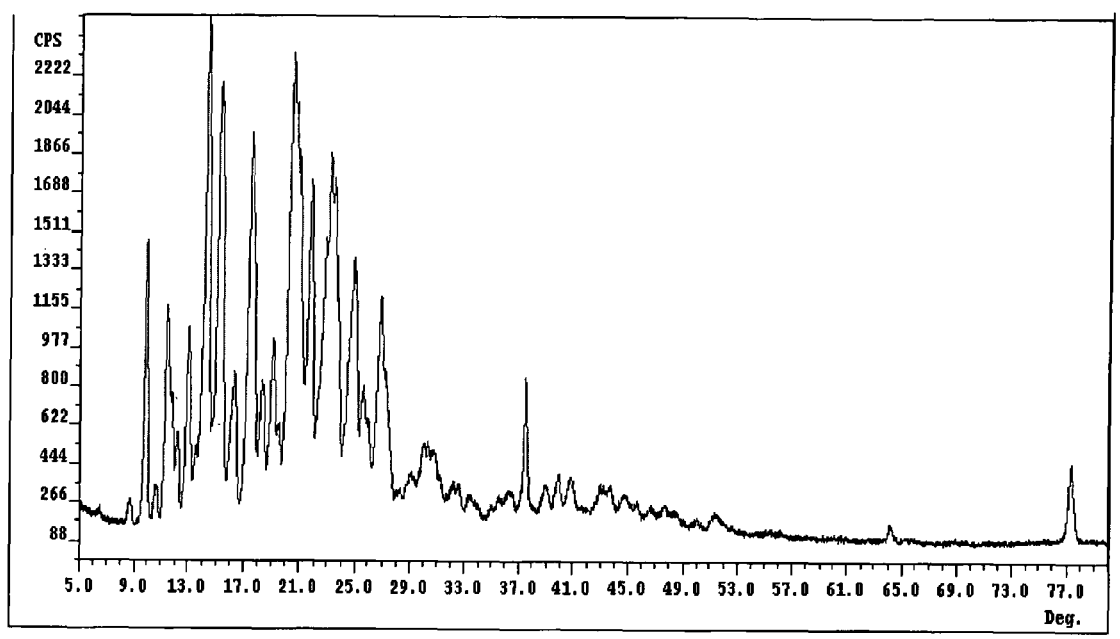
FIG. 4 is an x-ray diffraction pattern of imipramine pamoate Form IV.
Figure 9:
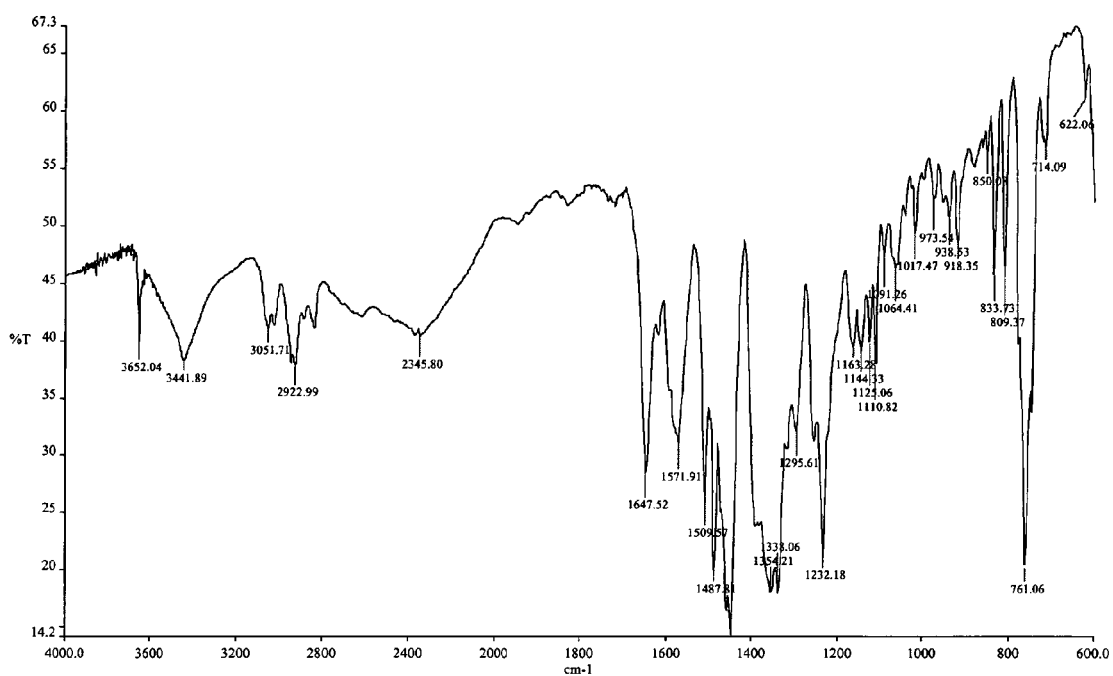
FIG. 9 is a Fourier Transform Infrared spectrum of imipramine pamoate Form IV.
Figure 14:
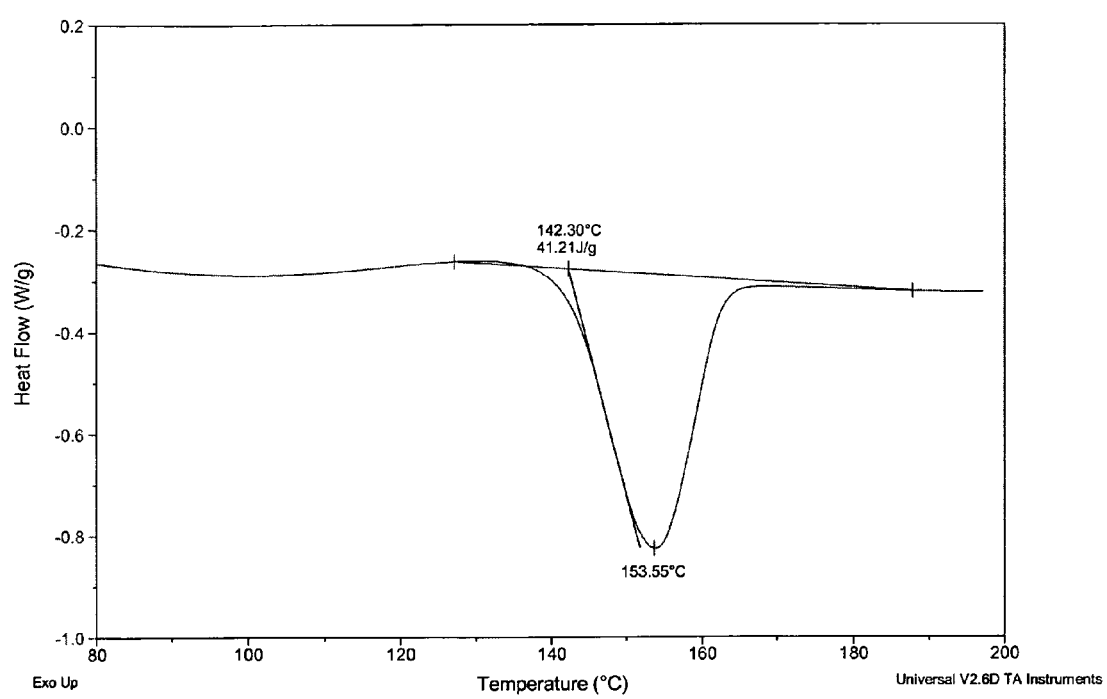
FIG. 14 is a differential scanning calorimetry thermogram of imipramine pamoate Form IV.

Imipramine pamoate Form IV is defined as having at least one characteristic, more preferably at least two characteristics selected from:

a) a phase transition as determined by DSC of 140-160° C.;

b) an x-ray diffraction pattern as of FIG. 4;

c) an infrared spectrum as of FIG. 9, d) a thermogram as measured by differential scanning calorimetry as of FIG. 14 exhibiting phase transition at about 140-160° C. with a heat of fusion of at least 18 Joules per gram and more preferably 38-45 Joules per gram; and e) prepared by the process of:
   i) combining imipramine pamoate Form III with a solvent or combination of solvents selected from water and short chain alcohols,
   ii) warming the reaction solution to about 70° C. until the polymorphic form appears
   iii) cooling and precipitating solids from the reaction mixture at a temperature less than 25° C.,
   iv) collecting the precipitated solids by filtration or centrifugation,
   v) washing the collected solids, and
   vi) drying the solids under vacuum at about 103° C. for a sufficient time to provide dry solids.

In one embodiment the Imipramine pamoate Form IV is prepared by the process consisting of:

i) combining imipramine pamoate Form III with a solvent or combination of solvents selected from water and short chain alcohols, ii) warming the reaction solution to about 70° C. until the polymorphic form appears iii) cooling and precipitating solids from the reaction mixture at a temperature less than 25° C., iv) isolating and purifying the sample, and v) drying the solids under vacuum at about 103° C. for at least 19 hours.

Figure 5:
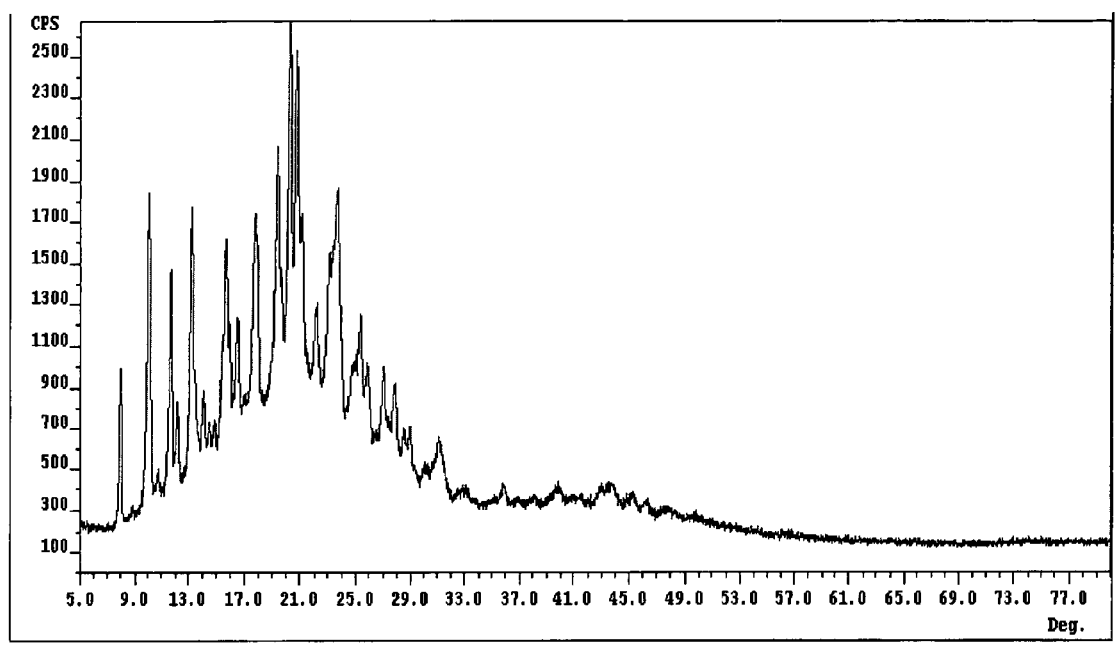
FIG. 5 is an x-ray diffraction pattern of imipramine pamoate Form V.
Figure 10:
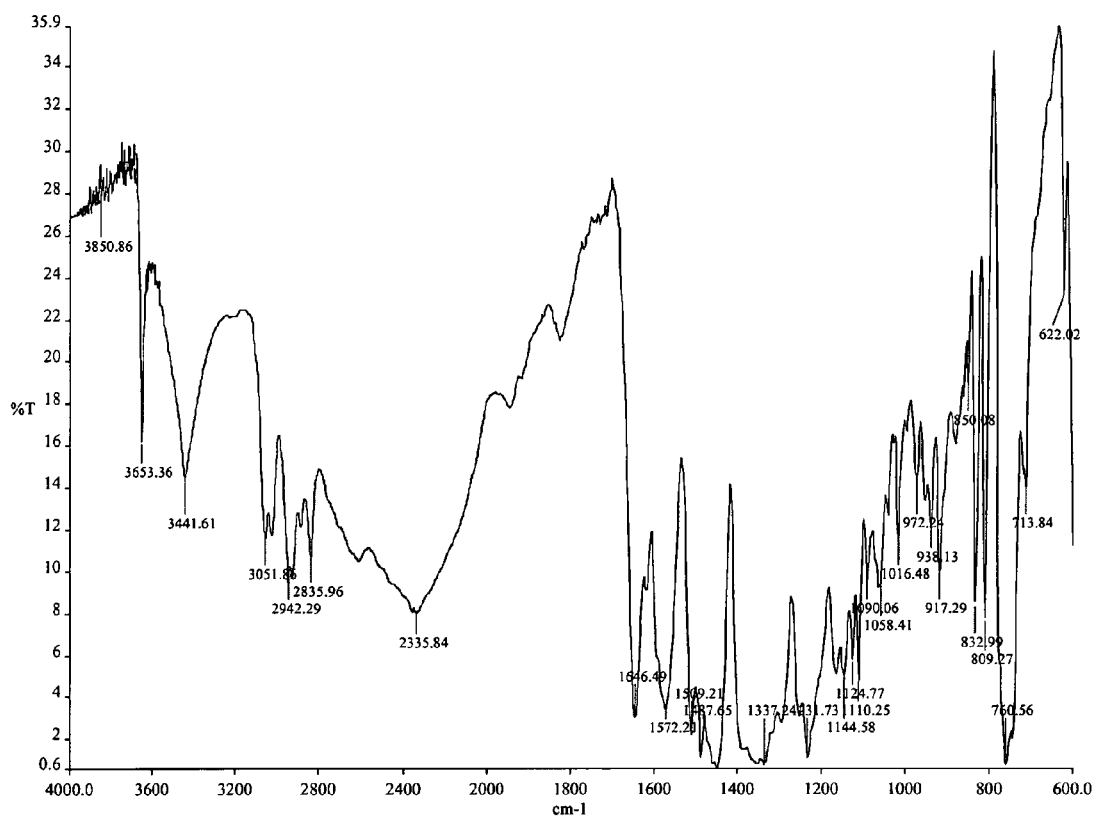
FIG. 10 is a Fourier Transform Infrared spectrum of imipramine pamoate Form V.
Figure 15:
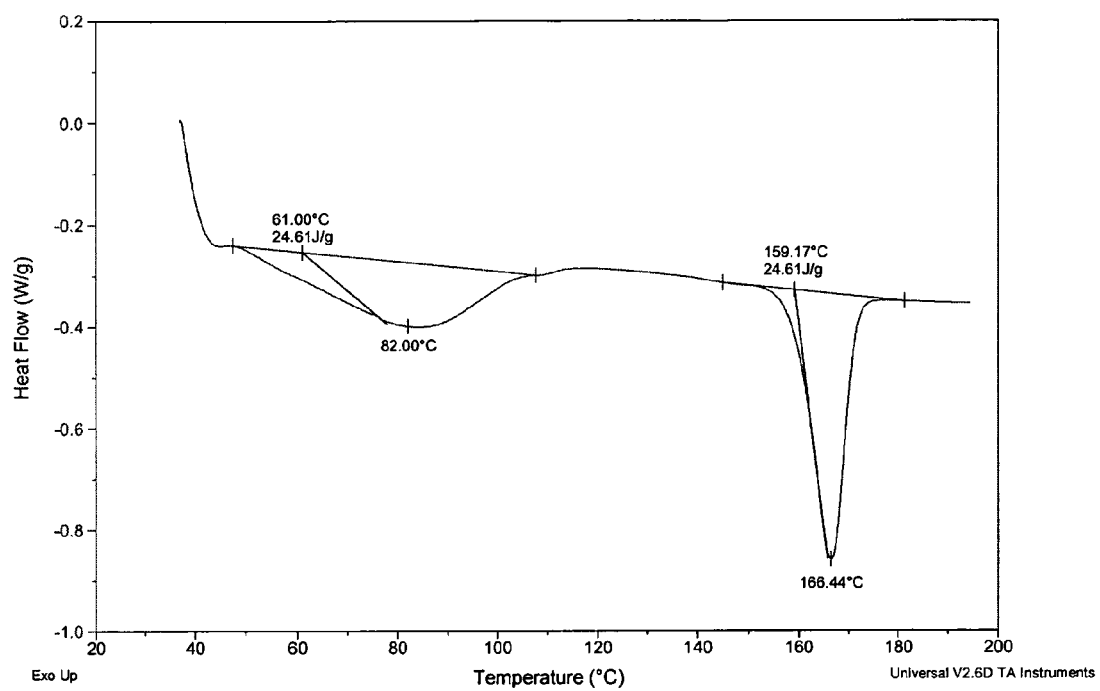
FIG. 15 is a differential scanning calorimetry thermogram of imipramine pamoate Form V.

Imipramine pamoate Form V is defined as a physical blend of 5-95 wt % Imipramine pamoate Form I and 5-95 wt % Imipramine pamoate Form III having at least one characteristic, more preferably at least two characteristics selected from:

a) an x-ray diffraction pattern as of FIG. 5;

b) an infrared spectrum as of FIG. 10, c) a thermogram as measured by differential scanning calorimetry as of FIG. 15 exhibiting phase transitions at about 60-110° C. and 150-170° C. with heats of fusion for each of at least 10 joules per gram and more preferably 20-28 Joules per gram; and d) prepared by the process of:
   i) preparing imipramine pamoate Form I and imipramine pamoate Form
   ii) combining 5-95 wt % imipramine pamoate Form I and 5-95 wt % imipramine pamoate Form III,
   iii) forming a homogenous mixture of the two forms (by mixing, blending, tumbling, rotating, or by other mechanical action), and
   iv) assessing the quality of the polymorphic blend by analytical methodology selected from differential scanning calorimetry (DSC), Infrared absorption (IR) and powder x-ray diffraction (PXRD).

Imipramine pamoate Form V is a blend of Imipramine pamoate Forms I-IV and VI. It is preferred that the blend comprise:

0-100 wt % of imipramine pamoate Form I, 0-100 wt % of imipramine pamoate Form II, 0-100 wt % of imipramine pamoate Form III, 0-100 wt % of imipramine pamoate form IV, and 0-100 wt % of imipramine pamoate form VI.

In one embodiment Form V comprises 20-80 wt % of imipramine pamoate Form I, and in another embodiment Form V comprises 40-60 wt % of imipramine pamoate Form I. In one embodiment Form V comprises 20-80 wt % of imipramine pamoate Form II, and in another embodiment Form V comprises 40-60 wt % of imipramine pamoate Form II. In one embodiment Form V comprises 20-80 wt % of imipramine pamoate Form III, and in another embodiment Form V comprises 40-60 wt % of imipramine pamoate Form III. In one embodiment Form V comprises 20-80 wt % of imipramine pamoate Form IV, and in another embodiment Form V comprises 40-60 wt % of imipramine pamoate Form IV. In one embodiment Form V comprises 20-80 wt % of imipramine Form VI, and in another embodiment Form V comprises 40-60 wt % imipramine pamoate Form VI. In a particular embodiment Form V comprises 5-95 wt % imipramine pamoate Form I and 5-95 wt % imipramine pamoate Form III.

Figure 18:
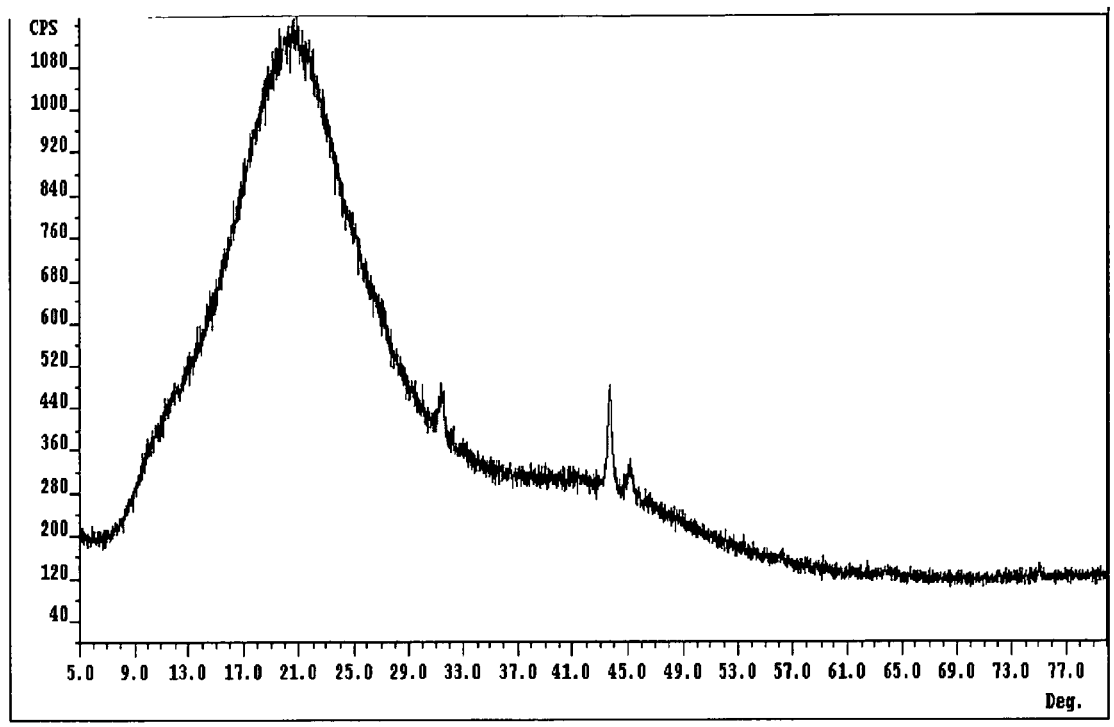
FIG. 18 is an x-ray diffraction pattern of another embodiment of a mixture of imipramine pamoate Form I and of imipramine pamoate Form VI.
Figure 19:
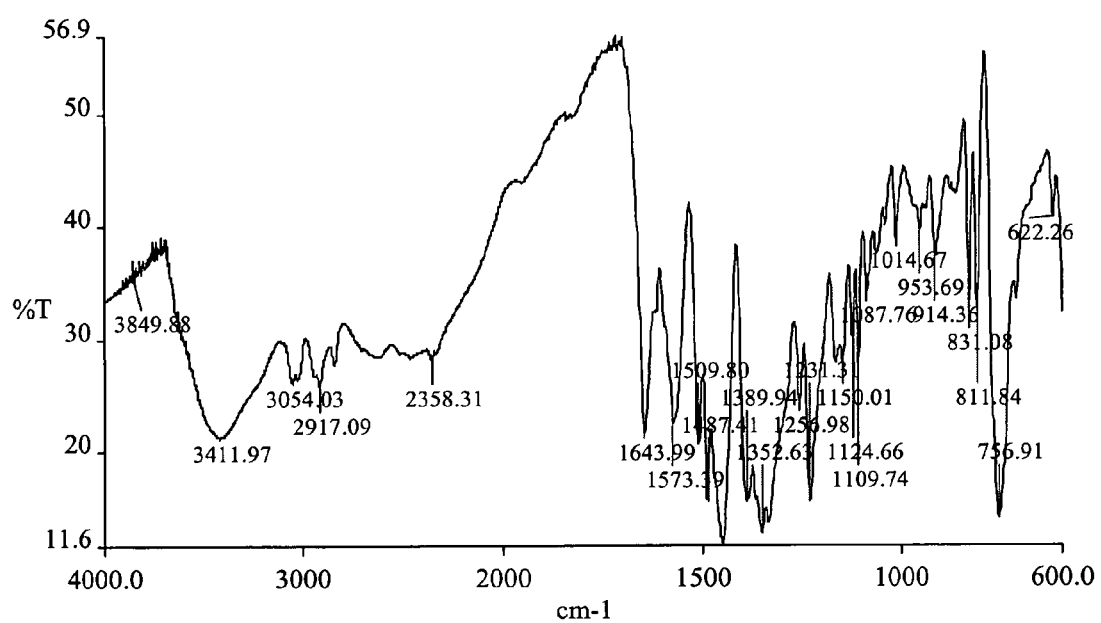
FIG. 19 is a Fourier Transform Infrared spectrum of a mixture of imipramine pamoate Form I and of imipramine pamoate Form VI.
Figure 20:
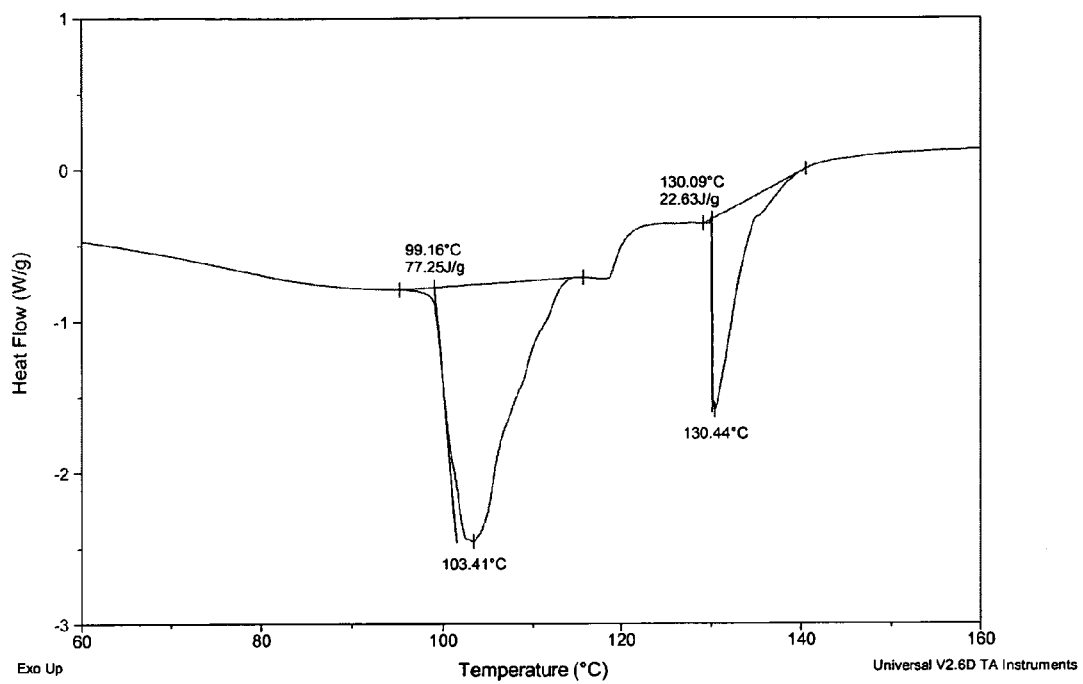
FIG. 20 is a differential scanning calorimetry thermogram of a mixture of imipramine pamoate Form I and of imipramine pamoate Form VI.
Figure 21:
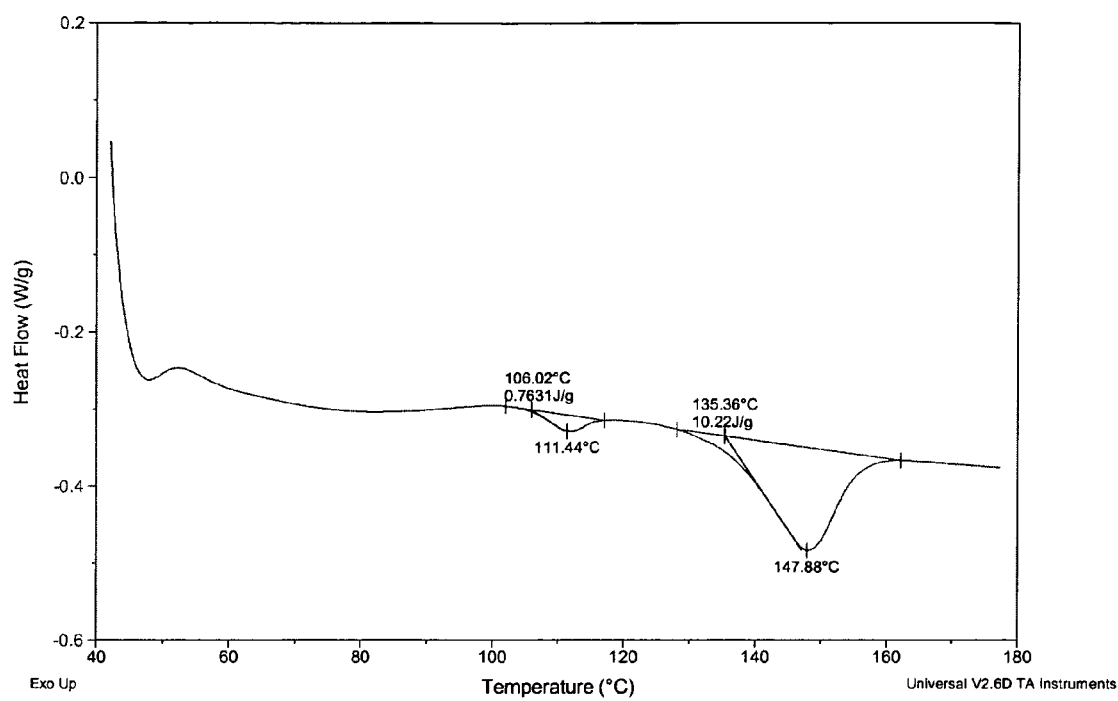
FIG. 21 is a differential scanning calorimetry thermogram of imipramine pamoate Form II after annealing.

Imipramine pamoate Form VI is defined as having at least one characteristic, more preferably at least two characteristics selected from:

a) phase transitions as determined by DSC of 98-118° C. and 128-145° C.;

b) an X-ray diffraction pattern as of FIG. 18;

c) an infrared spectrum as of FIG. 19;

d) a thermogram as measured by differential scanning calorimetry as of FIG. 20 exhibiting phase transition at about 98-118° C. and at about 128-145° C. and having associated heats of fusion of at least 50 and 8 Joules per gram, respectively; and e) prepared by the process comprising the steps of:
   i) adding the pH adjusted solution of imipramine hydrochloride in a gradual, metered manner to the pH adjusted solution of disodium pamoate,
   ii) warming the solution to about 42° C. until the polymorphic form appears,
   iii) cooling and precipitating the solids from the reaction mixture at a temperature less than about 25° C.,
   iv) collecting the precipitated solids by filtration or centrifugation,
   v) washing the collected solids, and
   vi) drying the solids.

In one embodiment the imipramine pamoate Form VI is prepared by the process consisting of the steps of:
   i) adding the pH adjusted solution of imipramine hydrochloride in a gradual, metered manner to the pH adjusted solution of disodium pamoate,
   ii) warming the reaction solution to about 42° C. until the polymorphic form appears,
   iii) cooling and precipitating solids from the reaction mixture at a temperature less than about 25° C.,
   iv) collecting the precipitated solids by filtration or centrifugation,
   v) washing the collected solids, and
   vi) drying the solids.

Specifically, each of the following experimental procedures is provided for Imipramine pamoate, forms I-VI. Detailed experimental procedures for the polymorph conversion/purification and crystallization processes are provided as follows:

Example I

Synthesis of Imipramine Pamoate Form I To a solution containing 34.86 g of disodium pamoate in 358.8 g of water was added a dilute NaOH solution to adjust the solution to about pH 9.4. To a second solution of 51.07 g of Imipramine HCl in 392.0 g of water was added a dilute NaOH solution to adjust the Imipramine solution to about pH 4.5. The Imipramine solution was added to the disodium pamoate solution over 3 h. The mixture was stirred and warmed to about 53° C. for 1.5 h. The mixture was cooled to <20° C. and solids were collected by filtration. The solid cake was washed with water. Relatively dry cake (96.66 g) was sampled. The sample was dried to yield a solid powder characterized by PXRD (FIG. 1), IR (FIG. 6) and DSC (FIG. 11). This material was designated as form I according to the following observations: form I (105-113° C., amorphous); form II (108-115° C. and 137-151° C.); form III (160-171° C.); form IV (140-160° C.), form V (physical blend), and form VI (process mixture).

Example 2

Synthesis of Imipramine Pamoate—(Form II)—To a solution containing 38.57 g of disodium pamoate in 424.0 g of water was added a dilute NaOH solution to adjust the solution to about pH 9.5. The disodium pamoate solution was adjusted to about pH 9.3 with dilute HCl solution. To a second vessel containing 56.81 g of imipramine HCl in 405.0 g of water was added a dilute NaOH solution to adjust the imipramine solution to about pH 4.5. The imipramine HCl solution was transferred to a metered addition funnel and was added to the disodium pamoate solution over about 52 min. The reaction mixture was stirred and heated at about 55° C. for approximately 8.75 h then cooled to <25° C. The solids were collected by filtration and the solid cake was washed with water. The imipramine pamoate collected was dried at about 93° C. for about 7-12 hours (33.22 g) and was characterized by PXRD (FIG. 2), IR (FIG. 7) and DSC (FIG. 12).

Example 3

Synthesis of Imipramine Pamoate—(Form III)—A mixture containing 50.2 g of imipramine pamoate (form II) in 10.0 g of water and 490.0 g of ethanol was stirred and heated to about 76° C. The reaction mixture was stirred and heated at about 76° C. for 4.25 h then cooled quickly to <25° C. The solids were collected by filtration and the solid cake was washed with water. Solids were transferred to a drying dish and dried at about 103° C. under vacuum for >12 h. Imipramine pamoate (47.7 g) was dried and was characterized by XRD (FIG. 3), IR (FIG. 8) and DSC (FIG. 13).

Example 4

Synthesis of Imipramine Pamoate—(Form IV)—A mixture containing 10.04 g of imipramine pamoate (form III) in 98.0 g of water and 2.0 g of ethanol was stirred and heated to about 70° C. The reaction mixture was stirred and heated at about 70° C. for 24 h then cooled quickly. The solids were collected by filtration and the solid cake was washed with water. Solids were transferred to a drying dish and dried at about 103° C. under vacuum for >19 h. imipramine pamoate (8.74 g) was characterized by PXRD (FIG. 4), IR (FIG. 9) and DSC (FIG. 14).

Example 5

Purification of Imipramine Pamoate—To a solution containing 34.92 g of disodium pamoate in 369.5 g of USP water was added a dilute solution of NaOH to adjust to pH 9.4. In another reactor, a dilute solution of NaOH was added to a solution containing 51.16 g of Imipramine HCl in 398.0 g of USP water to reach about pH 4.5. Imipramine pamoate seed (0.1 g) (form II) was added to the disodium pamoate solution. The Imipramine HCl solution was transferred to the disodium pamoate solution (about 26° C.) over 3.2 h. The mixture was heated from about 26° C. to 53° C. After 16 h, 20.0 g of ethyl acetate (EtOAc) was added to the mixture at about 53° C. The reactor was cooled to near 10° C. and stirred for 1.75 h. The solids were collected by filtration and washed with water followed by washing with a EtOAc-water mixture. Solids were dried at about 105° C. HPLC analysis (FIG. 17) indicated a decrease in the observed impurities compared with material prepared in the absence of organic solvent (FIG. 16).

Example 6

Admixtures of Form 1 and Form III in a multitude of ratios ranging from about 5% to 95% were prepared by adding each form in the desired amount to a common vessel and insuring visual homogenization by rotating, tumbling, stirring or agitating the mixing vessel. Aliquots of the blends were analytically characterized. Analyses by PXRD (FIG. 5), IR (FIG. 10) and DSC (FIG. 15) are provided as representative characterizations of the admixtures and identified as Form V. Specifically, the analyses reported herein result from testing of a blend comprising an approximately equal ratio of the two forms.

Example 7

Synthesis of Imipramine Pamaote—(Form VI)— A solution of disodium pamoate (43.88 g) in water (446.0 g) was prepared at a pH of about 9.5. A solution of imipramine HCl (63.38 g) in water (485.0 g) was prepared at a pH of about 4.0. The imipramine HCl solution (552.7 g) was added to the disodium pamoate solution at a controlled rate over a period of about 2.5 hours. After complete addition, the mixture was warmed to near 40-42° C. over approximately 4 h. Stirring was continued for approximately 3 additional hours at near 40-42° C. and then the solid product was isolated by filtration and washed with water. Imipramine pamoate (85.22 g) (92.6%) was isolated after drying at (78-80° C.). Throughout the heating process, samples were taken from the mixture and washed with water then dried. The Imipramine pamoate samples isolated at 42° C. (1.25 h) and 42° C. (2.25 h) contained a mixture of amorphous Imipramine Pamoate and Form VI. The Imipramine pamoate solid was characterized by PXRD (FIG. 18), FTIR (FIG. 19) and DSC (FIG. 20).

Example 8

Imipramine pamoate Form II was dried in a vacuum oven at 110° C. for 60 minutes as an annealing process. The material was characterized by DSC (FIG. 21). The thermogram indicated a significant decrease in the amount of amorphous content in Form II and the enhancement of the observed higher temperature transition.

The present invention has been described with particular reference to the preferred embodiments without limit thereto. One of skill in the art would realize additional embodiments, alterations and additions which are within the metes and bounds of the invention which is more specifically set forth in the claims appended hereto.

Claimed is:

1. An amorphous form of imipramine pamoate characterized by a differential scanning calorimetry (DSC) thermogram exhibiting a phase transition of about 105-113° C. and a heat of fusion of at least 0.5 joules per gram.

2. The amorphous form of imipramine pamoate of claim 1 wherein said thermogram exhibits a heat of fusion of 1-2 Joules per gram.

3. A process for preparing the imipramine pamoate of claim 1 comprising the steps of:
   a) combining the pH adjusted solutions of imipramine hydrochloride with disodium pamoate,
   b) warming the solution to about 53° C. for about 1-2 hours,
   c) cooling and precipitating solids from the reaction solution at a temperature less than about 20° C.,
   d) collecting the precipitated solids by filtration or centrigution,
   e) washing the collected solids, and
   f) drying the solids.

4. An amorphous form of imipramine pamoate of claim 1 characterized by an infrared (IR) absorbance spectrum as of FIG. 6.

5. A process for preparing the imipramine pamoate of claim 4 comprising the steps of:

a) combining the pH adjusted solutions of imipramine hydrochloride with disodium pamoate,
b) warming the solution to about 53° C. for about 1-2 hours,
c) cooling and precipitating solids from the reaction solution at a temperature less than about 20° C.,
d) collecting the precipitated solids by filtration or centrifugation,
e) washing the collected solids, and
f) drying the solids.

6. An amorphous form of imipramine pamoate of claim 1 characterized by a powder X-ray diffraction (PXRD) diffraction pattern as of FIG. 1.

7. A process for preparing the imipramine pamoate of claim 6 comprising the steps of:
a) combining the pH adjusted solutions of imipramine hydrochloride with disodium pamoate,
b) warming the solution to about 53° C. for about 1-2 hours,
c) cooling and precipitating solids from the reaction solution at a temperature less than about 20° C.,
d) collecting the precipitated solids by filtration or centrifugation,
e) washing the collected solids, and
f) drying the solids.

8. A polymorphic form of imipramine pamoate characterized by a differential scanning calorimetry (DSC) thermogram exhibiting phase transitions at about 108-115° C. and at about 137-151° C. and having associated heats of fusion of at least 0.5 Joules per gram and 8 Joules per gram respectively.

9. The polymorphic form of imipramine pamoate of claim 8 wherein said associated heats of fusion are 2-4 and 12-15 joules per gram, respectively.

10. A process for preparing the imipramine pamoate of claim 8 comprising the steps of:
a) adding the pH adjusted solution of imipramine hydrochloride in a gradual, metered manner to the pH adjusted solution of disodium pamoate,
b) warming the reaction solution to about 55° C. until the polymorphic form appears,
c) cooling and precipitating solids from the reaction mixture at a temperature less than about 25° C.,
d) collecting the precipitated solids by filtration or centrifugation,
e) washing the collected solids, and
f) drying the solids.

11. A polymorphic form of imipramine pamoate of claim 8 characterized by an infrared (IR) absorbance spectrum as of FIG. 7.

12. A process for preparing the imipramine pamoate of claim 11 comprising the steps of:
a) adding the pH adjusted solution of imipramine hydrochloride in a gradual, metered manner to the pH adjusted solution of disodium pamoate,
b) warming the reaction solution to about 55° C. until the polymorphic form appears,
c) cooling and precipitating solids from the reaction mixture at a temperature less than about 25° C.,
d) collecting the precipitated solids by filtration or centrifugation,
e) washing the collected solids, and
f) drying the solids.

13. A polymorphic form of imipramine pamoate characterized by a powder X-ray diffraction (PXRD) pattern as of FIG. 2.

14. A process for preparing the imipramine pamoate of claim 13 comprising the steps of:

a) adding the pH adjusted solution of imipramine hydrochloride in a gradual, metered manner to the pH adjusted solution of disodium pamoate,
b) warming the reaction solution to about 55° C. until the polymorphic form appears,
c) cooling and precipitating solids from the reaction mixture at a temperature less than about 25° C.,
d) collecting the precipitated solids by filtration or centrifugation, e) washing the collected solids, and
f) drying the solids.

15. A polymorphic form of imipramine pamoate characterized by a differential scanning calorimetry (DSC) thermogram exhibiting a phase transition of about 160-171° C. and a heat of fusion of at least 2 Joules per gram.

16. The polymorphic form of imipramine pamoate of claim 15 wherein said heat of fusion is about 35-55 Joules per gram.

17. A process for preparing imipramine pamoate of claim 15 comprising the steps:
a) preparing imipramine pamoate Form II,
b) combining imipramine pamoate Form II with a solvent or combination of solvents selected from water and short chain alcohols,
c) warming the reaction solution to about 76° C. until the polymorphic form appears,
d) cooling and precipitating solids from the reaction mixture at a temperature less than about 25° C.,
e) collecting the precipitated solids by filtration or centrifugation,
f) washing the collected solids, and
g) drying the solids.

18. A polymorphic form of imipramine pamoate of claim 15 characterized by an infrared (IR) absorbance spectrum as of FIG. 8.

19. A process for preparing imipramine pamoate of claim 18 comprising the steps:
a) preparing imipramine pamoate Form II,
b) combining imipramine pamoate Form II with a solvent or combination of solvents selected from water and short chain alcohols,
c) warming the reaction solution to about 76° C. until the polymorphic form appears,
d) cooling and precipitating solids from the reaction mixture at a temperature less than about 25° C.,
e) collecting the precipitated solids by filtration or centrifugation, f) washing the collected solids, and
g) drying the solids.

20. A polymorphic form of imipramine pamoate characterized by a powder X-ray diffraction (PXRD) pattern as of FIG. 3.

21. A process for preparing imipramine pamoate of claim 20 comprising the steps:
a) preparing imipramine pamoate Form II,
b) combining imipramine pamoate Form II with a solvent or combination of solvents selected from water and short chain alcohols,
c) warming the reaction solution to about 76° C. until the polymorphic form appears
d) cooling and precipitating solids from the reaction mixture at a temperature less than about 25° C.,
e) collecting the precipitated solids by filtration or centrifugation,
f) washing the collected solids, and
g) drying the solids.

22. A polymorphic form of imipramine pamoate characterized by a differential scanning calorimetry (DSC) thermogram exhibiting a phase transition at about 140-160° C. and a heat of fusion of at least 18 Joules per gram.

23. The polymorphic form of imipramine pamoate of claim 22 wherein said heat of fusion is 38-45 Joules per gram.

24. A process for preparing imipramine pamoate of claim 22 comprising the steps of:
a) combining imipramine pamoate Form III with a solvent or combination of solvents selected from water and short chain alcohols,
b) warming the reaction solution to about 70° C. until the polymorphic form appears
c) cooling and precipitating solids from the reaction mixture at a temperature less than about 25° C.,
d) collecting the precipitated solids by filtration or centrifugation, e) washing the collected solids, and
f) drying the solids.

25. A polymorphic form of imipramine pamoate of claim 22 characterized by an infrared (IR) absorbance spectrum as of FIG. 9.

26. A process for preparing imipramine pamoate of claim 25 comprising the steps of:
a) combining imipramine pamoate Form III with a solvent or combination of solvents selected from water and short chain alcohols,
b) warming the reaction solution to about 70° C. until the polymorphic form appears
c) cooling and precipitating solids from the reaction mixture at a temperature less than about 25° C.,
d) collecting the precipitated solids by filtration or centrifugation,
e) washing the collected solids, and
f) drying the solids.

27. A polymorphic form of imipramine pamoate characterized by a powder X-ray diffraction (PXRD) pattern as of FIG. 4.

28. A process for preparing imipramine pamoate of claim 27 comprising the steps of:
a) combining imipramine pamoate Form III with a solvent or combination of solvents selected from water and short chain alcohols,
b) warming the reaction solution to about 70° C. until the polymorphic form appears
c) cooling and precipitating solids from the reaction mixture at a temperature less than about 25° C.,
d) collecting the precipitated solids by filtration or centrifugation,
e) washing the collected solids, and
f) drying the solids.

29. A polymorphic blend of imipramine pamoate Form I and imipramine pamoate Form III characterized by a differential scanning calorimetry (DSC) thermogram exhibiting phase transitions of about 60-110° C. and at about 150-170° C. and each possessing a heat of fusion of at least 10 Joules per gram.

30. The polymorphic form of imipramine pamoate of claim 29 wherein said heats of fusion are 20-28 Joules per gram.

31. A process for preparing the polymorphic blend of claim 29 comprising the steps of:
a) preparing imipramine pamoate Form I and imipramine pamoate Form III,
b) combining imipramine pamoate Form I and imipramine pamoate Form III in a desired weight percentage of each component in a common vessel,
c) mixing, blending, tumbling, rotating, or by other mechanical action to insure and assure homogenous intermixing of imipramine pamoate Form I and imipramine pamoate Form III to form said polymorphic blend, and
d) assessing the quality of the polymorphic blend by analytical methodology selected from differential scanning calorimetry (DSC), Infrared absorption (IR) and powder x-ray diffraction (PXRD).

32. A polymorphic blend of imipramine pamoate Form I and imipramine pamoate Form III of claim 29 characterized by an infrared (IR) absorbance spectrum as of FIG. 10.

33. A process for preparing imipramine pamoate of claim 32 comprising the steps of:
a) preparing imipramine pamoate Form I and imipramine pamoate Form III,
b) combining imipramine pamoate Form I and imipramine pamoate Form III in a desired weight percentage of each component in a common vessel,
c) mixing, blending, tumbling, rotating, or by other mechanical action to insure and assure homogenous intermixing of imipramine pamoate Form I and imipramine pamoate Form III to form said polymorphic blend, and
d) assessing the quality of the polymorphic blend by analytical methodology selected from differential scanning calorimetry (DSC), Infrared absorption (IR) and powder x-ray diffraction (PXRD).

34. A polymorphic blend of imipramine pamoate Form I and imipramine pamoate Form III characterized by a powder X-ray diffraction (PXRD) pattern as of FIG. 5.

35. A process for preparing imipramine pamoate consistent with claim 34 comprising the steps of:
a) preparing imipramine pamoate Form I and imipramine pamoate Form III,
b) combining imipramine pamoate Form I and imipramine pamoate Form III in a desired weight percentage of each component in a common vessel,
c) mixing, blending, tumbling, rotating, or by other mechanical action to insure and assure homogenous intermixing of imipramine pamoate Form I and imipramine pamoate Form III to form said polymorphic blend, and
d) assessing the quality of the polymorphic blend by analytical methodology selected from differential scanning calorimetry (DSC), Infrared absorption (IR) and powder x-ray diffraction (PXRD).

36. A process for preparing purified forms of imipramine pamoate comprising the steps:
a) combining the pH adjusted solutions of imipramine hydrochloride and disodium pamoate at a metered or unmetered rate of combination,
b) adding an organic solvent to the reaction mixture during the reagent combining step or afterward,
c) warming the reaction solution to a temperature less than or equal to the added solvent's azeotropic boiling point,
d) cooling and precipitating solids from the reaction mixture,
e) collecting the precipitated solids by filtration or centrifugation,
f) optionally washing the collected solids with water, solvent or a mixture thereof,
g) drying the solids, optionally under vacuum at temperatures sufficient to remove the water and solvent, and
h) assessing the quality of the dried solid by chromatographic methods.

37. A process according to claim 36 whereby said solvent is water immiscible.

38. A process according to claim 36 whereby said solvent is water miscible.

39. A process according to claim 36 whereby said solvent is at least one solvent selected from lower carbon chain alkyl and/or aryl alcohols, esters, and ketones.

40. A blend of at least one imipramine pamoate polymorphic form with another form.

41. A blend according to claim 40 whereby at least one imipramine pamoate polymorphic form is blended with amorphous imipramine pamoate.

42. A process for preparing a mixture of polymorphic forms of imipramine pamoate comprising the steps of
   a) a process temperature change during the reaction between imipramine as its mineral acid salt with a solution of pamoic acid or its salt such that the temperature of reaction providing a lower phase transition form is increased to the temperature range which provides at least one second, higher melting polymorph, and
   b) the addition of a secondary solvent capable of allowing the reaction temperature to increase to that temperature where at least one additional polymorph is formed, and
   c) a process temperature change during drying of the isolated solids for the reaction mixture such that the temperature is increased for a time period required to produce at least one additional polymorph.

43. A process for preparing a mixture of polymorphic forms of imipramine pamoate comprising the steps of:
   a) preparing the individual forms to be blended selected from the group defined as Form I, Form II, Form III, Form IV, Form V and Form VI,
   b) combining the desired forms of imipramine pamoate in a pre-determined weight ratio of each component in a common vessel,
   c) mixing, blending, tumbling, rotating, or by other mechanical action to insure and assure homogenous intermixing of the two forms, and
   d) assessing the quality of the polymorphic blend by analytical methodology selected from differential scanning calorimetry (DSC), Infrared absorption (IR), powder x-ray diffraction (PXRD) and chromatographic methodology.

44. A polymorphic form of imipramine pamoate characterized by a differential scanning calorimetry (DSC) thermogram exhibiting phase transitions at about 98-118° C. and at about 128-145° C. and having associated heats of fusion of at least 50 and 8 Joules per gram, respectively.

45. The polymorphic form of imipramine pamoate of claim 44 wherein said heats of fusion are at least 30 and 5 joules per gram respectively.

46. The polymorphic form of imipramine pamoate of claim 44 wherein said heats of fusion are 73-82 and 18-27 joules per gram, respectively.

47. A process for preparing the imipramine pamoate of claim 44 comprising the steps of:
   a) adding the pH adjusted solution of imipramine hydrochloride in a gradual, metered manner to the pH adjusted solution of disodium pamoate,
   b) warming the reaction solution to about 42° C. until the polymorphic form appears,
   c) cooling and precipitating solids from the reaction mixture at a temperature less than about 25° C.,
   d) collecting the precipitated solids by filtration or centrifugation,
   e) washing the collected solids, and
   f) drying the solids.

48. A polymorphic form of imipramine pamoate of claim 44 characterized by an infrared (IR) absorbance spectrum consistent with and generally comparable to that represented by FIG. 19.

49. A process for preparing the imipramine pamoate of claim 48 comprising the steps of:
   a) adding the pH adjusted solution of imipramine hydrochloride in a gradual, metered manner to the pH adjusted solution of disodium pamoate,
   b) warming the reaction solution to about 42° C. until the polymorphic form appears,
   c) cooling and precipitating solids from the reaction mixture at temperature less than about 25° C.,
   d) collecting the precipitated solids by filtration or centrifugation,
   e) washing the collected solids, and
   f) drying the solids.

50. A polymorphic form of imipramine pamoate characterized by a powder X-ray diffraction (PXRD) pattern consistent with and generally comparable to that represented in FIG. 18.

51. A process for preparing the imipramine pamoate of claim 50 comprising the steps of:
   a) adding the pH adjusted solution of imipramine hydrochloride in a gradual, metered manner to the pH adjusted solution of disodium pamoate,
   b) warming the reaction solution to about 42° C. until the polymorphic form appears,
   c) cooling and precipitating solids from the reaction mixture at a temperature less than about 25° C.,
   d) collecting the precipitated solids by filtration or centrifugation,
   e) washing the collected solids, and
   f) drying the solids.

52. A synthetic process capable of producing multiple polymorphic forms of imipramine pamoate comprising at least one step selected from: isolating amorphous imipramine pamoate from the reaction vessel; isolating amorphous imipramine pamoate in combination with a selected polymorphic form of imipramine pamoate; isolating a single polymorphic form of imipramine pamoate and isolating a mixture of polymorphic forms of imipramine pamoate.

53. A synthetic process capable of inter-converting physical forms of imipramine pamoate comprising at least one step selected from subjecting amorphous imipramine pamoate to solvent and temperature conditions sufficient for generating an amount of polymorphic imipramine pamoate from 1-100% of the single polymorph; subjecting an imipramine pamoate polymorph exhibiting a lower phase transition temperature to solvent and temperature conditions sufficient for generating an amount of a second polymorphic form of imipramine pamoate from 1-100% and said second polymorphic form having a higher phase transition temperature and subjecting a mixture of amorphous imipramine pamoate and an imipramine pamoate polymorph exhibiting a lower phase transition temperature to solvent and temperature conditions sufficient for generating an amount of a second polymorphic imipramine pamoate from 1-100%, and said second polymorphic form having a higher phase transition temperature.

54. A pharmaceutical composition of at least one polymorphic form of imipramine pamoate suitable for use in treating depression, fibromyalgia, childhood nocturnal enuresis and adult urinary incontinence, trichotillomania, post-traumatic stress disorder, panic disorder and to provide analgesic-like relief for neuropathic pain wherein said pharmaceutical composition is a solid.

55. A pharmaceutical composition comprising a polymorphic form of imipramine pamoate comprising at least one material selected from the group consisting of imipramine pamoate Form I, imipramine pamoate Form II, imipramine pamoate Form III, imipramine pamoate Form IV and imipramine pamoate Form VI, adapted for use in treating depression, fibromyalgia, childhood nocturnal enuresis and adult urinary incontinence, trichotillomania, post-traumatic stress disorder, panic disorder and to provide analgesic-like relief for neuropathic pain wherein said pharmaceutical composition is a solid.

56. A pharmaceutical composition comprising 1 to 95% amorphous imipramine pamoate and 5-99 wt % of at least one material selected from imipramine pamoate Form II, imipramine pamoate Form III, imipramine pamoate Form IV and imipramine pamoate Form VI wherein said pharmaceutical composition is a solid.

57. A pharmaceutical composition according to claim 56 exhibiting resistance to ratio changes of the at least one polymorphic form of imipramine pamoate compared to the amorphous imipramine pamoate when subjected to time, temperature and humidity.

58. A pharmaceutical composition according to claim 56 and presented in a human dosage.

59. A process capable of inter-converting physical forms of imipramine pamoate at least one step selected from optionally subjecting amorphous imipramine pamoate to temperature conditions sufficient for generating an amount of polymorphic imipramine pamoate from 1-100% of the single polymorph; optionally subjecting an imipramine pamoate polymorph exhibiting a lower phase transition temperature to temperature conditions sufficient for generating an amount of a second polymorphic form of imipramine pamoate from 1-100% and said second polymorphic form having a higher phase transition temperature; optionally subjecting a mixture of amorphous imipramine pamoate and an imipramine pamoate polymorph exhibiting a lower phase transition temperature to temperature conditions sufficient for generating an amount of a second polymorphic imipramine pamoate from 1-100%, and said second polymorphic form having a higher phase transition temperature and optionally subjecting a mixture of amorphous imipramine pamoate and an imipramine pamoate polymorph to temperature conditions sufficient for substantially converting the amorphous imipramine pamoate to the said imipramine pamoate polymorph.

60. A process according to claim 59 wherein the mixture of amorphous imipramine pamoate and an imipramine pamoate polymorph contains at least one solvent and is dried to yield enhanced concentrations of the said polymorph.

61. A process according to claim 59 wherein a mixture of imipramine pamoate selected from amorphous, polymorphic and mixtures thereof is subjected to an annealing process to yield a purified polymorphic form.

62. A pharmaceutical composition comprising:
0-100 wt % of imipramine pamoate with a phase transition of about 105-133° C. and a heat of fusion of at least 0.5 joules per gram; 0-100 wt % of imipramine pamoate with a phase transition of about 108-115° C. with a heat of fusion of at least 0.5 joules per gram and a phase transition of about 137-151° C. with a heat of fusion of at least 8 joules per gram; 0-100 wt % of imipramine pamoate with a phase transition of about 160-171° C. and a heat of fusion of at least 20 joules per gram; 0-100 wt % of imipramine pamoate with a phase transition of about 140-160° C. and a heat of fusion of 18 joules per gram; 0-100 wt % of imipramine pamoate with a phase transition of about 60-110° C. with a heat of fusion of at least 15 joules per gram and a phase transition of about 150-170° C. with a heat of fusion of at least 15 joules per gram; and
0-100 wt % of imipramine pamoate with a phase transition of about 98-118° C. with a heat of fusion of at least 30 joules per gram and a phase transition of about 128-145° C. with a heat of fusion of at least 5 joules per gram wherein said pharmaceutical composition is a solid.

63. The pharmaceutical composition of claim 62 comprising 20-80 wt % of said imipramine pamoate with a phase transition of about 105-133° C. and a heat of fusion of at least 0.5 joules per gram.

64. The pharmaceutical composition of claim 62 comprising 40-60 wt % of said imipramine pamoate with a phase transition of about 105-133° C. and a heat of fusion of at least 0.5 joules per gram.

65. The pharmaceutical composition of claim 62 comprising 20-80 wt % of said imipramine pamoate with a phase transition of about 108-115° C. with a heat of fusion of at least 0.5 joules per gram and a phase transition of about 137-151° C. with a heat of fusion of at least 8 joules per gram.

66. The pharmaceutical composition of claim 62 comprising 40-60 wt % of said imipramine pamoate with a phase transition of about 108-115° C. with a heat of fusion of at least 0.5 joules per gram and a phase transition of about 137-151° C. with a heat of fusion of at least 8 joules per gram.

67. The pharmaceutical composition of claim 62 comprising 20-80 wt % of said imipramine pamoate with a phase transition of about 140-160° C. and a heat of fusion of at least 18 joules per gram.

68. The pharmaceutical composition of claim 62 comprising 40-60 wt % of said imipramine pamoate with a phase transition of about 140-160° C. and a heat of fusion of at least 18 joules per gram.

69. The pharmaceutical composition of claim 62 comprising 20-80 wt % of said imipramine pamoate with a phase transition of about 160-171° C. and a heat of fusion of at least 20 joules per gram.

70. The pharmaceutical composition of claim 62 comprising 40-60 wt % of said imipramine pamoate with a phase transition of about 160-171° C. and a heat of fusion of at least 20 joules per gram.

71. The pharmaceutical composition of claim 62 comprising 20-80 wt % of said imipramine pamoate with a phase transition of about 60-100° C. and a heat of fusion of at least 10 joules per gram and a phase transition of about 150-170° C. and a heat of fusion of at least 10 joules per gram.

72. The pharmaceutical composition of claim 62 comprising 40-60 wt % of said imipramine pamoate with a phase transition of about 60-100° C. and a heat of fusion of at least 10 joules per gram and a phase transition of about 150-170° C. and a heat of fusion of at least 10 joules per gram.

73. The pharmaceutical composition of claim 62 comprising 20-80 wt % of said imipramine pamoate with a phase transition of about 98-118° C. and a heat of fusion of at least 30 joules per gram and a phase transition of about 128-145° C. and a heat of fusion of at least 5 joules per gram.

74. The pharmaceutical composition of claim 62 comprising 40-60 wt % of said imipramine pamoate with a phase transition of about 98-118° C. and a heat of fusion of at least 30 joules per gram and a phase transition of about 128-145° C. and a heat of fusion of at least 5 joules per gram.

75. The process of claim 53 wherein the said second imipramine pamoate polymorph exhibits a higher polymorphic purity than the material subjected to the process conditions.

76. The process of claim 53 wherein the said second imipramine pamoate polymorph exhibits a higher chemical purity than the material subjected to the process conditions.

77. The process of claim 59 wherein an imipramine pamoate polymorph produced exhibits a prominent phase transition occurring at about 137-151° C. and having an associated heat of fusion of at least about 8 joules per gram.

78. The process of claim 59 wherein an imipramine pamoate polymorph produced exhibits phase transitions at about 100-120° C. and at about 137-151° C. and having associated heats of fusion of at least about 0.5 and 8 joules per gram, respectively.

79. The process of claim 59 wherein an imipramine pamoate polymorph produced exhibits a higher polymorphic purity than the material subjected to the process conditions.

* * * * *